US008768628B2

(12) United States Patent
Ghedan et al.

(10) Patent No.: US 8,768,628 B2
(45) Date of Patent: Jul. 1, 2014

(54) RISE IN CORE WETTABILITY CHARACTERIZATION METHOD

(76) Inventors: Shawket Ghedan, Abu Dhabi (AE); Celal Hakan Canbaz, Abu Dhabi (AE)

( * ) Notice: Subject to any disclaimer, the term of this patent is extended or adjusted under 35 U.S.C. 154(b) by 395 days.

(21) Appl. No.: 13/271,238

(22) Filed: Oct. 12, 2011

(65) Prior Publication Data

US 2012/0136578 A1 May 31, 2012

Related U.S. Application Data

(60) Provisional application No. 61/394,782, filed on Oct. 20, 2010.

(51) Int. Cl.
*G01N 15/08* (2006.01)

(52) U.S. Cl.
USPC .................... 702/12; 166/50; 166/335

(58) Field of Classification Search
CPC ........................................ G01N 15/08
USPC ............................................. 702/12
See application file for complete search history.

(56) References Cited

U.S. PATENT DOCUMENTS

| | | | | |
|---|---|---|---|---|
| 3,910,350 A | * | 10/1975 | Mastroianni | 166/400 |
| 4,154,301 A | * | 5/1979 | Carlin et al. | 166/401 |
| 5,069,065 A | * | 12/1991 | Sprunt et al. | 73/152.09 |
| 5,962,139 A | * | 10/1999 | Hagiwara et al. | 428/413 |
| 6,207,013 B1 | * | 3/2001 | Oriaran et al. | 162/111 |
| 2002/0022579 A1 | * | 2/2002 | Griffith et al. | 507/220 |
| 2004/0000905 A1 | * | 1/2004 | Freedman et al. | 324/303 |
| 2005/0216223 A1 | * | 9/2005 | Lenormand et al. | 702/138 |
| 2006/0132131 A1 | * | 6/2006 | Fleury et al. | 324/307 |
| 2007/0062258 A1 | * | 3/2007 | Egermann et al. | 73/38 |
| 2008/0150524 A1 | * | 6/2008 | Song et al. | 324/303 |
| 2010/0285999 A1 | * | 11/2010 | Norman et al. | 507/240 |
| 2010/0329072 A1 | * | 12/2010 | Hagan et al. | 366/163.2 |
| 2011/0106456 A1 | * | 5/2011 | Szabo et al. | 702/30 |
| 2011/0272325 A1 | * | 11/2011 | Soane et al. | 208/14 |

OTHER PUBLICATIONS

Carlos A. Grattoni, Efstathios D. Chiotis & Richard A. Dawe (Determination of Relative Wettability of Porous Sandstones by Imbibition Studies; J. Chem. Tech. Biotechnol. 1995, 64, 17-24).*

* cited by examiner

*Primary Examiner* — Sujoy Kundu
*Assistant Examiner* — Alvaro Fortich
(74) *Attorney, Agent, or Firm* — Barry Choobin; Patent 360 LLC

(57) ABSTRACT

The various embodiments herein provide a method for determining core wettability characteristics of reservoir rock samples based on modified form of Washburn equation. The method involves saturating a core sample with a first reservoir fluid such as water and imbibing with a second reservoir fluid such as oil. The change in square of the core mass with respect to time is monitored during an imbibition process to acquire a data to calculate a contact angle to determine the wettability of the sample. The contact angle is calculated by using the modified form of Washburn equation. A single or twin core sample is used to calculate the wettability characteristics. The method measures wettability characteristics in terms of contact angle and not in terms of wettability index.

15 Claims, 26 Drawing Sheets

RISE IN CORE WETTABILITY CHARACTERIZATION METHOD

BACKGROUND

The present invention is sponsored by The Petroleum Institute of Abu Dhabi.

1. Technical Field

The embodiments herein generally relate to a method of characterization or determination of wettability of reservoir rock. The embodiments herein more particularly relate to a new technique for determining the wettability of reservoir rock samples using Washburn Equation for calculating the contact angles.

2. Description of the Related Art

Reservoir wettability is one of the most important parameters, which directly control the fluid flow by having an effect on the location and distribution of the fluids. It also has an influence on core analyses such as capillary pressure, relative permeability, irreducible water and residual oil saturation and indirectly influences electrical properties of reservoir rocks. The wettability of reservoir rock influences many aspects of reservoir performance, particularly water-flooding and enhanced oil recovery techniques. This makes the understanding and accurate determination of the wettability of any oil reservoir very crucial for optimizing oil recovery.

Wettability is the relative preference of a solid surface to be coated by a certain fluid in a system. In a rock/oil/brine system, it is a measure of the preference that the rock surface has for an oil or water. When the rock is water-wet, there is a tendency for water to contact the majority of the rock surface. Similarly, in an oil-wet system, the rock is preferentially in contact with the oil; the location of the two fluids is reversed from the water-wet case, oil will contact the majority of the rock surface. When the rock surface does not display a preference for oil or water contact, intermediate wettability exists. Cases where water coats the surface of small pores while oil coats the surface of large pores are fractional wet or mixed wet, if continuous paths of oil and water wet rock are present.

Reservoir wettability is one of the most important parameters that control many aspects of the performance and quantification of hydrocarbon reservoirs. The validity of laboratory core analyses depends largely on the degree to which the test core represents the reservoir. If the wettability of the test core is not the same as that of the reservoir, then the measured parameters of capillary pressure, relative permeability, irreducible water saturation, residual oil saturation, and prediction of water flooding performance are inaccurate. Interpretation of water saturation from resistivity logs by Archie's method requires an accurate value of saturation exponent, in, which wettability influences. The possibility of applying an enhanced oil recovery method is related to the oil saturation remaining in the reservoir and its areal and vertical distribution, as well as its microscopic continuity in the pores network of the reservoir. The original wetting properties of the reservoir and its distribution play an important role in the choice of improved recovery processes to be applied. Accordingly, a knowledge of reservoir wettability is a significant asset in the decision making process concerning many different aspects of oil production.

Wettability of a reservoir rock can range from strongly water-wet to strongly oil-wet, and in between (intermediate wet) if the rock has no strong preference for either oil or water. The wetting conditions are strongly affected by the following factors: rock mineralogy, constituents and conditions of the pore surfaces, reservoir oil and formation water, adsorption or deposition of oil constituents on the rock surface, oil composition and reservoir conditions. Reservoir rocks are complex structures and often comprise a variety of mineral types of different wettability characteristics. Clean sandstone or quartz is extremely water-wet; sandstone reservoir rock is commonly moderately water-wet. Carbonates tendency is towards intermediate to oil-wet. Equilibrium between the constituents and conditions of the pore surfaces, the reservoir oil and formation water influences decide the reservoir wetting preferences. Variations in wettability are related to the thickness of the water film separating oil and reservoir rock during the oil displacement process. If stable thick water films separate the oil from the rock, the system will be water-wet. Thin water films (increasing height above free water level) can rupture allowing oil to contact the rock surface. Adsorption or deposition of oil constituents on the rock surface such as the polar oil components also affects the wetting conditions. Asphaltenes are candidates for wettability alteration to an oil wet state due to their polar groups that may interact and bind to the mineral surface. The polar compounds in resins and asphaltenes combine hydrophilic and hydrophobic characteristics, which are wettability-altering components in the oil phase. In relation to oil composition, Black-oil composition determines the solubility of the polar components. A crude oil that is a poor solvent for its own surfactants has a greater propensity to change wettability than one that is a good solvent. The Reservoir Conditions such as reservoir temperature, pressure and saturation history affect reservoir wettability.

The realization that rock wettability can be altered by adsorbable crude oil components led to the idea that heterogeneous or fractional wettability exist in reservoir rock. In fractional wettability, crude oil components are adsorbed in certain areas of the rock, so a portion of the rock is oil-wet, while the rest is strongly water-wet. Note that this is conceptually different from intermediate wettability, which assumes that all portions of the rock surface have a slight but equal preference to wetting by water or oil. Mixed wettability is a special type of fractional wettability. Unlike the fractional wettability, the oil-wet surfaces in mixed wettability assume specific locations and form continuous paths through the larger pores while the smaller pores remain water-wet and contain no oil.

Regardless of the rock mineralogy, hydrocarbon reservoir rocks are likely water wet before oil migration. They may change their wetting preference thereafter. The reservoir's saturation history influences the reservoir wetting preference and the degree of these wetting preferences. In a thick (100's of feet) oil-bearing formation, wettability can vary with depth, with a greater water-wetting preference near the bottom of the transition zone and a greater oil-wetting preference near the top. The higher zones have a greater capillary pressure, which can counteract the disjoining pressure and destabilize the water film, allowing surface-active components in the oil to contact the solid. In the lower structures, the solid surfaces mostly retain the water film.

Both quantitative and qualitative methods are in use for determining the wettability of a system. Qualitative methods investigate different criteria to determine the degree of water or oil wetness including imbibition rates, relative permeability curves, permeability/saturation relationships, capillary pressure curves and reservoir logs. Quantitative methods, on the other hand, try to quantify wettability by either determining the wettability angles or through some wettability indices. Some of the common quantitative wettability tests available in the industry include: Amott Wettability Method, USBM Wettability Method, Combined Amott-Harvey and USBM Wettability Method and Contact Angle Method.

Amott Wettability Method is commonly used technique to measure wettability of core samples. Amott wettability is the ratio of saturation change by spontaneous imbibition to the saturation change by both spontaneous imbibition and forced displacement. Amott method combines both capillary and viscous force effects to measure the average wettability of the core samples. A core sample is prepared by centrifuging under oil until irreducible water saturation (Swirr), placed into a water-filled tube where water spontaneously imbibes over a period of time (10-20 days) until attaining equilibrium. The sample is placed in a flow cell for forced displacement of oil by water until reaching residual oil saturation (Sor). The process is then reversed for spontaneous and forced oil imbibition, driving the water out of the core sample until reaching irreducible water saturation (Swirr). Separate ratios of spontaneous imbibition to total saturation change for water, $I_w$, and oil, $I_o$, are termed the water and oil imbibition indices, respectively. Preferentially water-wet cores have a positive displacement-by-water ratio and a zero value for the displacement-by-oil ratio. The displacement by-water ratio approaches +1 as the water wetness increases. Similarly, oil-wet cores have a positive displacement-by-oil ratio and a zero displacement-by-water ratio. Both ratios are zero for neutrally wet cores. The Amott-Harvey index, $I_{AH}$, combined the two ratios ($I_w$ and $I_o$) into a single wettability index. It is defined as the difference between the water spontaneous imbibition ratio, $I_w$, and that of the oil, $I_o$, ($I_{AH}=I_w-I_o$). The result is a number between +1 (strongly water-wetting) and −1 (strongly oil-wetting). If the oil ratio ($I_o$) has positive value and the water ratio ($I_w$) is zero, then the core is preferentially oil wet. Contrary to this, when the water ratio ($I_w$) has positive value and the oil ratio ($I_o$) is zero, it means that the core sample is preferentially water wet. If both values are zero, then the core is neutrally wet. The main problem with the Amott wettability test and its modifications is its insensitivity near neutral wettability. The test measures the ease with which the wetting fluid can spontaneously displace the non-wetting one. However, neither fluid will spontaneously imbibe and displace the other when the contact angle varies from roughly 60 to 120°. In addition, the limiting contact angle above which spontaneous imbibition will not occur depends on the initial saturation of the core.

USBM Wettability Method is an alternative quantitative method for determining the wettability index by using the hysteresis loop of capillary pressure curves. The USBM test also measures the average wettability of the core. USBM wettability test is faster than Amott test and it is more sensitive near neutral wettability. On the other hand, the USBM test cannot determine whether a system has fractional or mixed wettability, while the Amott test is sometimes sensitive to this wettability state. In some fractional- or mixed-wet systems, both water and oil will imbibe freely. The Amott method will have positive displacement by-water and displacement-by-oil ratios, indicating that the system is non-uniformly wetted. During the USBM test, a centrifuge spins the core sample at stepwise-increasing speeds. The sample starts at irreducible water saturation (Swirr) in a water filled tube. After spinning for some period of time at several spin rates, the sample reaches residual oil saturation (Sor) and it is placed into an oil-filled tube for another series of measurements. The areas under each of the capillary-pressure curves and the zero capillary-pressure line are calculated, and the logarithm of the ratio of the water-increasing to oil-increasing areas gives the USBM wettability index. The measurement range extends from +∞ (strongly water wetting) to −∞ (strongly oil wetting), although most measurement results are in a range of +1 to −1.

The basis of the Amott-Harvey index is relative changes in saturation, while the USBM index is a measure of the energy needed to make the forced displacement, making them related but independent indicators of wettability. Sharma and Wunderlich proposed a method by combining the Amott-Harvey and USBM methods and by modifying the USBM method, using a centrifuge rather than flooding with water and oil to obtain the forced flooding states. There are two advantages of the combined USBM/Amott method over the standard USBM method. They improved USBM resolution by accounting for the saturation changes that occur at zero capillary pressure and a data to enable a calculation of the Amott, Amott-Harvey and the USBM indices.

FIG. 1 shows a prior art illustrating a graph showing the steps of the Combined Amott-Harvey and USBM Wettability Methods. With respect to FIG. 1, the graph shows five steps of the method. They are: initial oil drive (1), spontaneous (free) imbibition of brine (2), brine drive (3), spontaneous (free) imbibition of oil (4) and oil drive (5). The areas under the brine- and oil-drive curves $A_1$ and $A_2$ provide the USB Mindex, while the Amott index uses the volumes of free and total water and oil displacements.

The contact angle testing methods measure the wettability of a mineral surface in contact with a fluid from the reservoir. Different methods of contact angle measurement exist in the oil industry. The Sessile Drop and the Modified Sessile Drop are two popular contact angle methods. In both the methods, a mineral crystal is mounted in a test cell comprising entirely of inert materials to prevent contamination. The Sessile Drop method uses a single flat and polished mineral crystal. The modified sessile drop method uses two flat and polished mineral crystals mounted parallel to each other on adjustable posts. Because a sandstone is primarily composed of quartz and limestone of calcite, a crystal of quartz or calcite simulates the pore surfaces of the reservoir rock. After cleaning, the surface is aged with formation brine. A drop of crude oil is placed in contact with the aged surface. The contact angle (θ), of the fluid on the mineral surface determines the intrinsic wettability of a reservoir rock. With a range of 0° to 180°, low angles are water wet while high angles are oil wet. In the 1980s, the Thin Layer Wicking method was developed for measuring the contact angles of all minerals, even with irregular shapes, such as no swelling clays, talc, dolomite, limestone, calcite, silicates and the cuboids hematite. In this method, a thin layer of powdered solid sample is deposited on glass slide. This facilitates penetration of the liquid into the layer and a sharp visible progressing contact angle line is visible. However, the Thin Layer Wicking method is limited to powdered rock samples and is not applicable for representing the wettability characteristics of reservoir rocks that have heterogeneous mineralogical composition.

Treiber et. al. used the water advancing contact angle to estimate the wettability of 55 oil reservoirs. In Treiber's et. al. study deoxygenated synthetic formation brine and dead anaerobic crudes were tested on quartz and calcite crystals at reservoir temperature. Contact angles (measured through the water) from 0° to 75° were deemed water-wet, 75° to 105° intermediate wettability, and 105° to 180° oil-wet. Although the range of wettabilities was divided into three regions, it should be strongly emphasized that these are arbitrary divisions. The wettability of different reservoirs can vary within the broad spectrum from strongly water-wet to strongly oil-wet.

Morrow described two initial conditions as reference and non-reference for calculating the cut-off values by using an advancing and receding contact angle and spontaneous imbibition data. For Instance, by using an Imbibition Curvature Ratio vs Intrinsic contact angle plot, the limiting value between water wet and intermediate zones is described as 62°. Similarly, the cut-off values for advancing contact angle is described as 0° to 62° for water wet region, 62° to 133° for Intermediately wet zone, and 133° to 180° for Oil wet zone.

Chilingar and Yen conducted an extensive research work on 161 limestone, dolomitic limestone, calcitic dolomite, and dolomite cores and classified the cut-off values for strongly oil wet (160° to 180°), oil wet (100° to 160°), intermediate wet (80° to 100°), water wet (80° to 20°), and strongly water wet (80° to 20°).

Using the Amott-Harvey index, $I_{AH}$, Cuiec stated that the system is water-wet when $+0.3 \leq I_{AH} \leq -1$, intermediate wet when $-0.3 < I_{AH} < 0.3$, and oil-wet when $-1 \leq I_{AH} \leq -0.3$. The measurement range of the USBM test method extends from $+\infty$ (strongly water wetting) to $-\infty$ (strongly oil wetting). The system would be diagnosed as water wet when the USBM index is near +1, intermediately wet when it is near 0 and oil wet when it is near −1. The USBM index was further subdivided and classified as follows, neutral or mixed wet (−0.1 to +0.1), slightly water wet (+0.1 to +0.3), water wet (+0.3 to +1.0), slightly oil wet (−0.1 to −0.3) and oil wet (−0.3 to −1.0).

Many of the wettability measurements are imprecise, particularly near neutral wettability. One method may show that a core is mildly oil-wet, while another shows that the core is mildly water-wet. The main problem with the Amott wettability test and its modifications is that they are insensitive near neutral wettability. The test measures the ease with which the wetting fluid can spontaneously displace the non-wetting one. However, neither fluid will spontaneously imbibe and displace the other, when the contact angle varies from roughly 60 to 120°. In addition, the limiting contact angle above which spontaneous imbibition will not occur depends on the initial saturation of the core. Moreover, the Amott method is rather very slow requiring many experimental steps.

USBM testing method is faster than the Amott test and is more sensitive near neutral wettability. However, the USBM test cannot determine whether a system has fractional or mixed wettability, while the Amott test is sometimes sensitive to that. Both the USBM test and the Amott test have serious weakness with respect to discriminating between systems that fall within the wettability range of 0° to 55°. Drainage curves in the contact angle range of 0° to 55° are not significantly affected by wettability but there is systematic decrease in imbibition capillary pressure with increase in contact angle. If trapping of the non-wetting phase is complete $I_w$ be unity, because forced displacement is not expected to reduce the trapped residual non-wetting phase, except at high capillary numbers. Thus, the Amott index does not discriminate between systems, which attain residual non-wetting phase without change in sign of imbibition capillary pressure. A comparable problem arises with the USBM test.

Although contact angle methods measure wettability directly, but there are some limitations. The contact angle cannot take into account the heterogeneity of the rock surface. Contact angles are measured on a single mineral crystal, while a core contains many different constituents. Furthermore, the wettability of clays in the reservoir cannot be examined with this method, as the contact angles are measured on flat smooth and shiny rock surface. Experimentally, it is generally found that a liquid drop on a surface can have many different stable contact angles. There is hysteresis in the contact-angle measurements. The reported contact angles are either the water-advancing or water receding contact angles. The advancing angle, $\theta_{adv}$, is measured by pulling the periphery of a drop over a surface, while the receding contact angle. $\theta_{rec}$; is measured by pushing it back. The difference $\theta_{adv} - \theta_{rec}$, is the contact-angle hysteresis and can be greater than 60°. Another important limitation of the contact angle method is that the required length of equilibration time cannot be reproduced in the lab. This may lead to problems such as erroneous classification of wetting state and sometimes to reproducibility issues. One other obvious limitations of wettability characterization using contact angle measurement is the absence of a standard reference. Consequently, except at the end point wetting states, the classification of wetting state from contact angle measurement is arbitrary and subjective.

Although it covers all wettability ranges sufficiently, the contact angle wettability testing methods are seldom utilized due to the many limitations. In addition to the limitations, the Amott and USBM testing methods are very demanding in terms of experimental setup and procedure. Moreover, the handling of the core samples to achieve the different parts of the tests may risk an alteration of the wettability during a testing. Additionally, Amott-Harvey and USBM reports wettability in terms of an index rather the contact angles.

These limitations call for a need of a new method for characterization of wettability that requires much simpler experimental setup, requires less experimental effort to perform, determines wettability in all possible ranges and finally determines wettability in terms of a contact angle rather than on a wettability index.

The above mentioned shortcomings, disadvantages and problems are addressed herein and which will be understood by reading and studying the following specification.

OBJECTIVES OF THE EMBODIMENTS

The primary object of the embodiments herein is to provide a method of characterization of wettability of fluids that is relatively quick, accurate and much simpler to construct and much faster to perform.

Another object of the embodiments herein is to provide a method of characterization of wettability of fluids that enables to measure wettability in terms of contact angle rather than on wettability index.

Yet another object of the embodiments herein is to provide a method of characterization of wettability of fluids that employs the Washburn Equation for dynamic determination of contact angles.

Yet another object of the embodiments herein is to provide a new wettability testing technique that is easy to use and requires no complex equipment.

Yet another object of the embodiments herein is to provide a method of characterization of wettability of fluids that is much easier to analyze and interpret than traditional methods.

Yet another object of the embodiments herein is to provide a new wettability testing technique that can effectively measure wettability of any set of reservoir fluid, any type of reservoir rock and at any heterogeneity level.

Yet another object of the embodiments herein is to provide a method of characterization of wettability of fluids that characterizes wettability across a board range of conditions i.e. from strongly water, to water wet, to neural wet, to oil wet, to strongly oil wet conditions.

These and other objects and advantages of the embodiments herein will become readily apparent from the following detailed description taken in conjunction with the accompanying drawings.

SUMMARY

The various embodiments provide a new wettability characterization technique or method. The technique is called the Rise in Core (RIC) wettability characterization technique. The RIC method is based on a modified form of the Washburn equation. The technique enables relatively quick and accurate measurements of wettability in terms of contact angle. The method, according to the embodiments herein, is easy to use and requires no complex equipment.

According to one embodiment herein, the Washburn Equation is employed for the dynamic determination of contact angles. The method is applicable for any set of reservoir fluids, on any type of reservoir rock and at any heterogeneity level. The method herein characterizes wettability across the board from strongly water, to water wet, to neural wet, to oil wet and to strongly oil wet conditions.

According to one embodiment herein, in a method for determining wettability of reservoir rock samples, core samples are generated by dividing a core plug into an average diameter of 3.8 cm and length of 1.5 cm. The sides of the core samples are sealed by an epoxy resin to ensure a one-dimensional liquid penetration into the core sample. A hook is mounted on topside of the core sample. After saturating the core sample with the first reservoir fluid, the core sample is connected to a high precision balance using a thin rope. The second reservoir fluid is contained in the imbibition beaker. The core sample is hanged with a thread over the imbibition liquid wherein a bottom part of the core sample barely touches the imbibition liquid. The imbibition process of the core sample with the imbibition liquid is commenced. The change in mass of the core sample over a period of time is monitored to obtain a data. The value of contact angle $\theta$ is calculated using the data obtained and the wettability is determined based on the value of the calculated contact angle.

According to one embodiment herein, to be able to apply the modified Washburn equation, one needs to determine its constant, C. This constant is a characteristic of the reservoir rock. To determine C, a cleaned and dried twin core sample (saturated with air now) is subjected to imbibition from a reference fluid of low surface energy. The change of the square of the core mass with respect to time is monitored using a high precision balance as the imbibition process starts. Since the reference fluid completely wets the core sample in the presence of air, the contact angle is assumed to be zero. Knowing the contact angle, and the square of mass with respect to time, the equation could be applied to determine the constant, C for the porous media under consideration.

According to an embodiment herein, the method is used for a Rock/liquid/liquid System.

According to an embodiment herein, twin core samples are saturated with one reservoir fluid and are subjected to imbibition from a second reservoir fluid. As the imbibition process takes place, the weight of core samples changes continuously due to the adjustments in the relative saturations of the two fluids. The square of the mass of the core with respect to time is monitored using a high precision balance. The data is acquired and analyzed with modified Washburn equation to determine the wettability of core.

The wettability is determined on the basis of calculated contact angle. The core sample is completely water wet at 0°, weakly water wet to weakly oil wet between 62° to 133°, completely oil wet at 180° and neutral at 90°.

According to an embodiment herein, a modified form a Washburn equation for a Rock/liquid/liquid System is derived from a Washburn equation provided for calculating a penetration rate for a liquid/air/rock system.

The step of deriving the modified form of the Washburn equation for a Rock/liquid/liquid System comprises acquiring a Washburn equation for a rock/liquid/liquid system, and wherein Washburn equation for a rock/liquid/liquid system is represented by $$t = \frac{\mu}{C \cdot \rho^2 \gamma \cos\theta} \cdot m^2, \tag{1}$$

wherein equation (1) is a Washburn equation for liquid/air/rock system, and wherein t is a penetration rate of a liquid into a porous sample, and wherein $\mu$ is a viscosity of the liquid, and wherein $\rho$ is a density of the liquid, and wherein $\gamma$ is a surface tension of the liquid, and wherein $\theta$ is a contact angle made by the liquid, and wherein m is a mass of the liquid penetrated into the porous sample and wherein C is a Constant of Characterization of the porous sample;

evaluating a value of $\gamma_{os}$ using a young's equation for a rock surface/oil/air system and a value of $\gamma_{ws}$ using a young's equation for a rock surface/water/air system and wherein the young's equation for a liquid/liquid/rock system is represented by equation (2)

$$\gamma_{ow} \cos\theta = \gamma_{os} - \gamma_{ws} \tag{2},$$

wherein $\gamma_{ow}$ is a surface tension between oil and water system, and wherein $\gamma_{os}$ is a surface tension between oil and solid system, and wherein $\gamma_{ws}$ is a surface tension between water and solid system;

substituting the evaluated value of $\gamma_{os}$ using a young's equation for a rock surface/oil/air system and value of $\gamma_{ws}$ using a young's equation for a rock surface/water/air system and substituting in equation (2) to obtain an equation (3), and wherein the equation (3) is $$\cos\theta_{wo} = \frac{(\gamma_o \cos\theta_o) - (\gamma_w \cos\theta_w)}{\gamma_{wo}}; \tag{3}$$

rearranging equation (1) to factor out $\gamma_{LV}$ to obtain an equation (4), and wherein $\gamma_{LV}$ is a liquid-vapor surface tension, and $$\gamma_{LV} = \frac{\mu}{C \cdot \rho^2 \cdot \cos\theta} \cdot \frac{m^2}{t}; \tag{4}$$

realizing that $\gamma_{LV}$ (liquid-vapor surface tension) is equivalent to $\gamma_o$ (oil-air surface tension), or $\gamma_w$ (water-air surface tension), substitute equation 4 in equation 3 and cancelling out similar terms to obtain equation (5), and wherein equation (5) is $$\cos\theta_{wo} = \frac{\left(\frac{m^2 \cdot \mu_o}{C\rho_o^2 t}\right) - \left(\frac{m^2 \cdot \mu_w}{C\rho_w^2 t}\right)}{\gamma_{wo}}; \tag{5}$$

wherein $\gamma_{LV}$ is liquid-vapor surface tension, and wherein $\gamma_o$ is oil-air surface tension and wherein $\gamma_w$ is water-air surface tension, and wherein $\mu_o$ is viscosity of oil, and wherein $\mu_w$ is viscosity of water, and wherein $\cos\theta_{wo}$ is contact angle between water and oil;

representing a relation ship between a mass of water imbibed into the core sample and a mass of oil imbibed in the core sample with a equation (6), wherein the equation (6) is $\rho_w g V_w = \rho_o g V_o$;

wherein $\rho_w$ is density of water and $V_w$ is volume of water imbibed, wherein $\rho_o$ is density of oil and $V_o$ is volume of oil imbibed, wherein the amount of water imbibed and amount of oil imbibed under gravity are same; and wherein air behaves as a strong non-wetting phase in both of a oil/air/solid and a water/air/solid systems, thereby indicating that both oil and water behaves as a strong wetting phases, resulting in an equal air/oil and air/water capillary forces for a same porous media and for a given pore size distribution, and wherein a mass change of a core sample due to a water imbibition is equal to a mass change of a core sample as a due to an oil imbibition because water or oil penetration of the porous media at any time is a function of a balance between a gravity and a capillary forces, and wherein a mass of water imbibed into a core sample is approximately equal to a mass of oil imbibed in the core sample core samples of a same rock type and dimensions, and for equal capillary forces;

cancelling out g in equation (6) represented $\rho_w g V_w = \rho_o g V_o$ to obtain an equation (7), wherein equation (7) is $\rho_w V_w = \rho_o V_o$ to acquire an equation (8), and wherein equation (8) is $$m_w = m_o \quad (8),$$

wherein $m_w$ is mass of water and wherein $m_o$ is mass of oil; factoring out $C \cdot m^2/t$ from equation (5) to obtain equation (9), wherein equation (9) is a modified Washburn equation, and wherein the modified Washburn equation is $$\cos\theta_{12} = \frac{(\mu_1 \cdot \rho_2^2) - (\mu_2 \cdot \rho_1^2)}{\rho_1^2 \rho_2^2 \cdot C \cdot \gamma_{L2L1}} \cdot \frac{m^2}{t}.$$

wherein $\theta_{12}$ is the contact angle of liquid/liquid/rock system, and wherein $\mu_1$ is a Viscosity of oil phase, and wherein $\mu_2$ is a Viscosity of water phase, and wherein $\rho_1$ is a density of oil phase in g/cm³, and wherein $\rho_2$ is a density of water phase in g/cm³, and wherein m is a mass of fluid penetrated into a porous rock in g, and wherein t is a time in min, and wherein $\gamma_{L2L1}$ is a surface tension between a oil and a water in dyne/cm, and C is a Characteristic Constant, of the porous rock.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

DETAILED DESCRIPTION OF THE EMBODIMENTS

Figure 1:
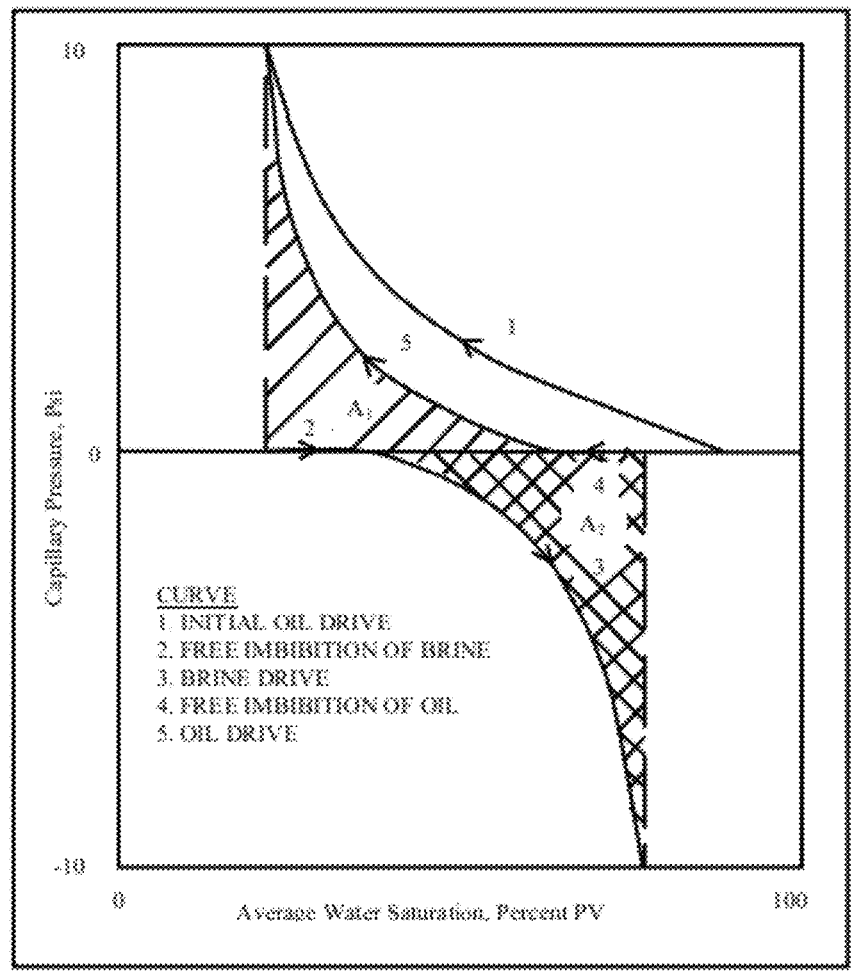
FIG. 1 shows a prior art illustrating a graph showing the steps of the Combined Amott-Harvey and USBM Wettability Methods.

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The following nomenclature is used to describe the various embodiments herein.

C=Constant, Characterization of the porous Material
g=Gravity, kg m/s$^2$
h=Height of the column of liquid, cm
m=Mass of fluid penetrated into the porous medium, g
r=Pore mean radius, μm
$R_c$=Radius of area open to imbibition, cm
t=time, min
V=Liquid Volume, cm$^3$
ΔP=Pressure Difference, psi
π=Pi Number
γ=Facial Tension, dyne/cm
$γ_{LV}$=Surface Tension between liquid and vapor phases, dyne/cm
$γ_{SO}$=Adhesion Tension between solid surface and oil phase, dyne/cm
$γ_{SW}$=Adhesion Tension between solid surface and water phase, dyne/cm
$γ_O$=Adhesion Tension between solid surface and water phase, dyne/cm
$γ_W$=Adhesion Tension between solid surface and water phase, dyne/cm
μ=Viscosity, cp
$μ_O$=Viscosity of oil phase, cp
$μ_W$=Viscosity of water phase, cp
ρ=Density, g/cm$^3$
$ρ_O$=Density of oil phase, g/cm$^3$
$ρ_W$=Density of water phase, g/cm$^3$
θ=Contact Angle, °
$θ_o$=Oil/Air Contact Angle, °
$θ_w$=Water/Air Contact Angle, °
$θ_{wo}$=Water/Oil Contact Angle, °
Φ=Porosity The embodiments herein provide a new wettability testing method. The new wettability testing method is known as "Rise in Core" (RIC) Wettability Characterization Technique. The method presented herein employs the Washburn Equation for dynamic determination of contact angle. The method is used for any sets of reservoir fluids. The method is used for different types of reservoir rock and for any heterogeneity level. The method herein characterizes the wettability of reservoir fluids across a broad range of conditions wherein the conditions ranging from a strongly water, to water wet, to neutral wet, to oil wet and to strongly oil wet conditions.

According to an embodiment herein, a method for determining core wettability characteristics comprises generating a core sample wherein the core sample is generated by dividing a core plug into a plurality of core samples of preset size and wherein the preset size of each core sample in the plurality of core samples is an average diameter of 3.8 cm and a length of 1.5 cm. A side of the core sample is sealed by an epoxy resin and wherein the side of the core sample is sealed to ensure a one-dimensional liquid penetration into the core sample, mounting a hook on a top side of the core sample. The core sample is saturated with a first reservoir fluid. The saturated core sample is connected to a high precision balance and wherein the saturated core sample is connected using a thin rope. A second reservoir fluid is taken in an imbibition beaker. The saturated core sample is hanged over the second reservoir fluid contained in the imbibition beaker and wherein the saturated core sample is hanged using a thread and the saturated core sample is hanged in a way such that a bottom part of the saturated core sample barely touches the second reservoir fluid. Then an imbibition process is commenced for the hanged and saturated core sample. A change in square of a mass of the hanged and saturated core sample over a period of time is monitored to obtain a data. A value of a contact angle θ is calculated using the obtained data and wherein the value of the contact angle θ is calculated by applying a modified form of Washburn equation. The wettability of the hanged core sample is determined using the calculated value of contact angle θ.

The technique of calculating the value of contact angle θ by applying the modified form of Washburn equation comprises a step of determining a value of a constant used in the Washburn equation and wherein the constant is a characteristic of a porous core sample.

The step of determining the constant comprises generating a twin core sample, saturating the twin core sample with air and imbibing the saturated twin core sample with a reference fluid and wherein the reference fluid has low surface energy. A change of a square of mass of the twin core sample with respect to a time (m$^2$/t), is calculated and monitored and wherein the change of a square of a core mass of the twin core sample with respect to time is monitored using a high precision balance and a computer. A value of the constant for the porous core sample is determined by applying the calculated value of the m$^2$/t and applying a value of the contact angle θ in the modified Washburn equation. The value of contact angle θ is assumed to be zero since the reference fluid completely wets the core sample in presence of air.

The first reservoir fluid is water. The second reservoir fluid is oil. The change in mass over a period of time (m$^2$/t) is monitored using a computer. The sample is a reservoir rock sample. The reservoir rock sample is completely water wet at a contact angle of 0°, weakly water wet to weakly oil wet between the contact angles of 62° to 133°, completely oil wet at a contact angle of 180° and neutral at a contact angle of 90°.

According to an embodiment herein, a method for determining a wettability characteristics of reservoir core samples comprising the steps of generating a twin core sample, cleaning the generated twin core sample, drying the cleaned twin core sample, saturating the dried twin core sample with a first reservoir fluid, imbibing the saturated twin core sample with a second reservoir fluid, monitoring a change of a square of a core mass of the twin core rock sample with respect to a time (m$^2$/t) to acquire a data, applying the acquired data in the modified Washburn equation and determining the wettability characteristics of the twin core rock sample.

Figure 2:
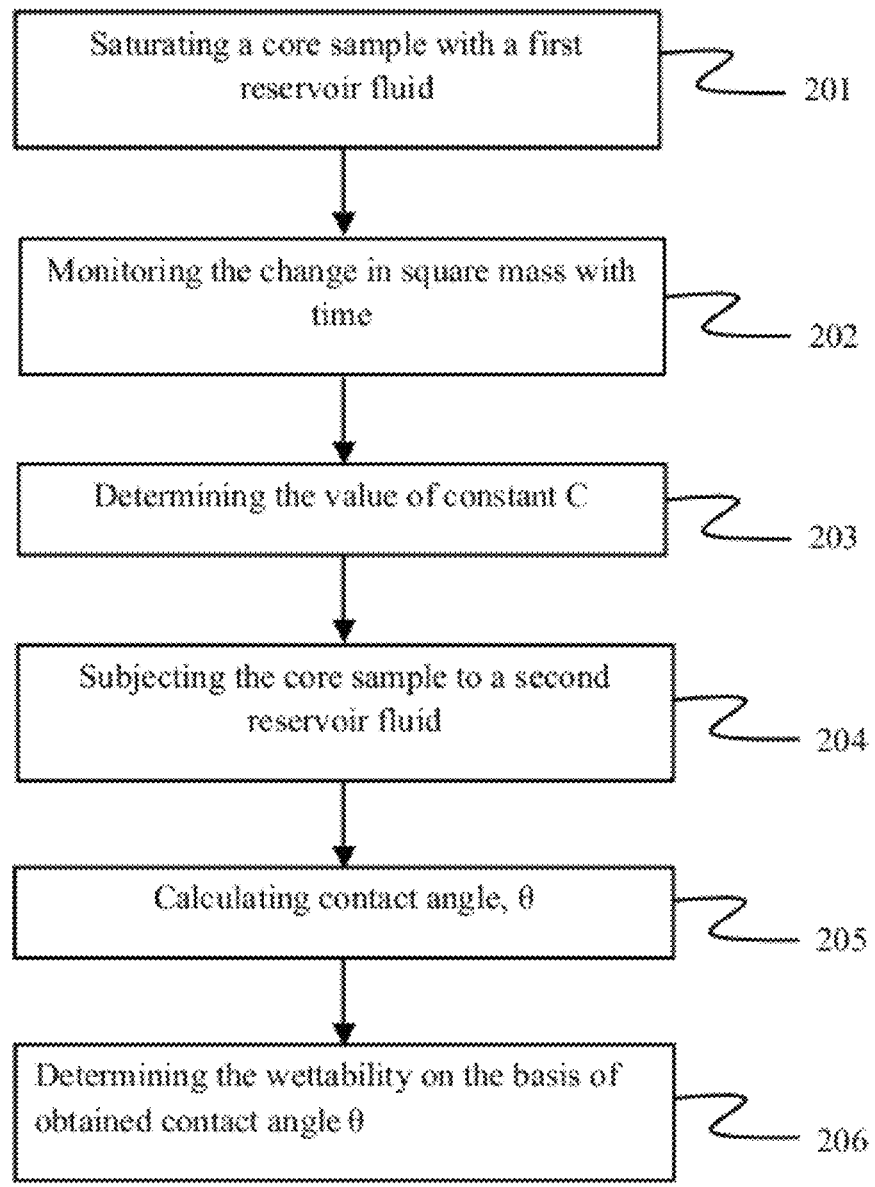
FIG. 2 illustrates a flow chart explaining the various steps of the method of characterization of the reservoir core samples, according to an embodiment herein.

FIG. 2 illustrates a block diagram showing the various steps of the method of characterization of the reservoir core samples, according to an embodiment herein. With respect to FIG. 2, the core sample is first saturated with a first reservoir fluid (201). The change in square mass with respect to time is monitored (202). An imbibition curve is obtained. Slope of the curve is calculated. Using the value of slope of dodecane/air/rock system, and knowing that dodecane spreads over the rock surface completely and has a contact angle of zero, the value of constant C is determined (203). Knowing the C, a twin core sample, saturated with one reservoir fluid (say oil), is subjected to the second reservoir fluid (say water). The slope of imbibition curves, the contact angle, θ, is calculated (205). The contact angle is calculated using the Washburn equation. The wettability of the core sample is determined on the basis of the obtained value of contact angle (206). The core sample is completely water wet at 0°, weakly water wet to weakly oil wet between 62° to 133°, completely oil wet at 180° and neutral at 90° in terms of water wettability and oil wettability.

Figure 3:
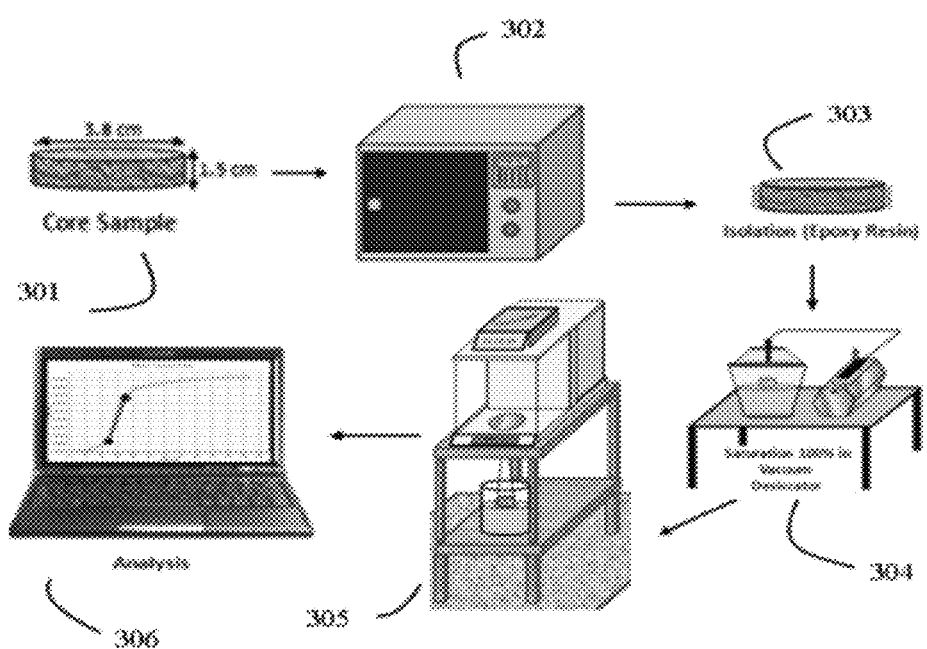
FIG. 3 shows a block diagram of an experimental setup of the Rise in Core wettability testing method, according to an embodiment herein.

FIG. 3 schematically shows an experimental setup of the Rise in Core wettability testing method, according to an embodiment herein. With respect to FIG. 3, Core plugs are divided into 3-4 core samples 301, each of 3.8 cm average diameter and 1.5 cm in length. The samples are then dried in oven 302. The sides of the samples are sealed by epoxy resin 303 to ensure one-dimensional liquid penetration into the core by the imbibition process. A hook is mounted on the top side of the core sample. A vacuum desiccator and a vacuum pump 304 are used to 100% saturate the core samples with different fluids. The RIC experiment setup 305 is composed of beaker to host the imbibing liquid. A thin rope was used to connect the core sample to a high precision balance (0.001 gm accuracy). After positioning the hanging core sample with the bottom part of the sample barely touching the imbibing fluid in the beaker the imbibition process is commenced, changing the relative saturation in the core samples, and eventually it's mass. A computer 306 continuously monitors the changing mass of the core sample versus time. Plots of squared mass change with time graphs are generated to calculate the contact angle.

Washburn Equation is proved to be very useful in attaining the contact angle of powder with gas/liquid system. It is further extended to determine the wettability of powder with liquid-liquid system, by combining the measurement as gas-liquid 1 and gas-liquid 2 systems and determine that of liquid 1-liquid 2 system. In the embodiments herein, the Washburn Equation is extended for application in a rock/liquid/liquid system. This paved the way to come up with a new technique to determine reservoir wettability through calculating the contact angle of reservoir rock/oil/formation water system. The new method is given the name of Rise in Core, RIC wettability characterization method.

Liquids are driven and penetrated into a naturally porous medium by capillary forces. For a liquid/Air/rock system, Washburn derived a mathematical formula to represent the penetration rate of the liquid into a porous media. The formula is presented as equation (1) as follows:

$$t = \frac{\mu}{C \cdot \rho^2 \gamma \cos\theta} \cdot m^2 \quad (1)$$

Here, C is a constant characterizing the porous media. To apply this equation to any liquid/air/rock system, the value of C has to be known. To determine the constant C, a reference liquid of low surface energy is utilized. An imbibition experiment is performed on Reference liquid/Air/rock sample. A change in mass of the rock sample is monitored as function of time. Since the reference liquid is assumed to spread over the rock surface completely, the contact angle, θ, is assumed to be zero. Having the physical properties of this liquid, such as Viscosity (μ), Density (ρ), surface tension (γ), the constant C of the rock sample is determined. Now if another imbibition experiment is performed on the same or twin core sample, the wettability of this rock sample could be determined for the new liquid/air/rock system.

Figure 4A:
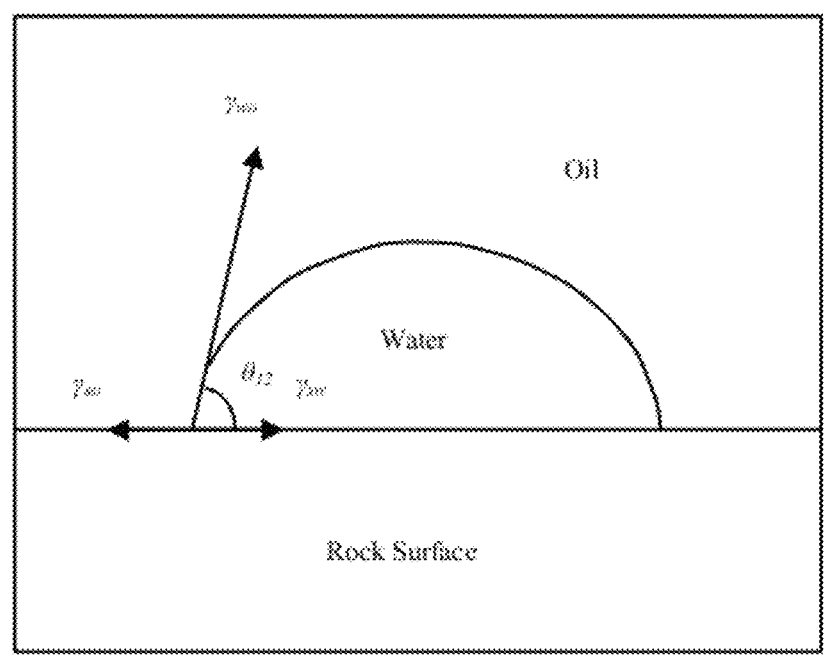
FIG. 4A shows a representation of young's equation with respect to an oil/water/rock surface system, according to an embodiment herein.
Figure 4B:
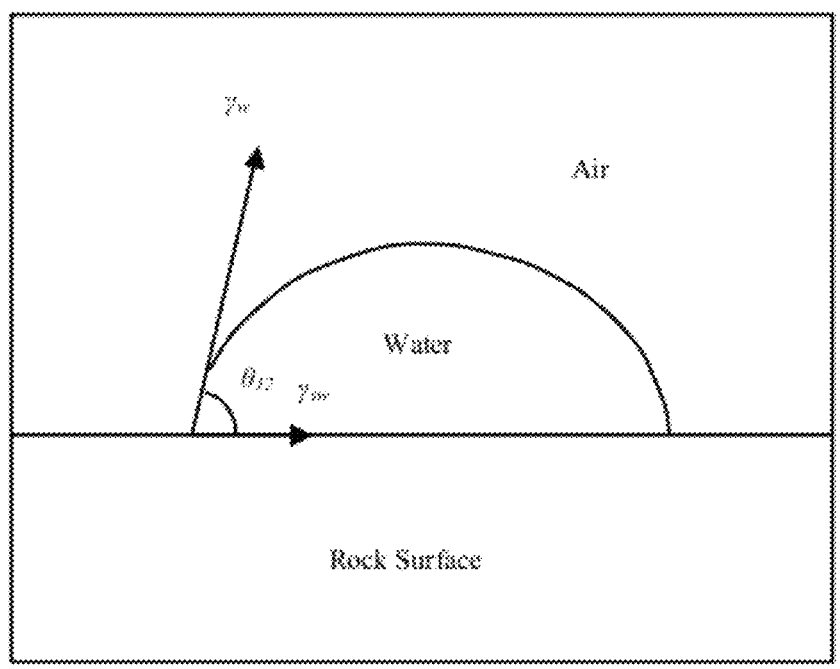
FIG. 4B shows are presentation of young's equation with respect to an air/water/rock surface system, according to an embodiment herein.
Figure 4C:
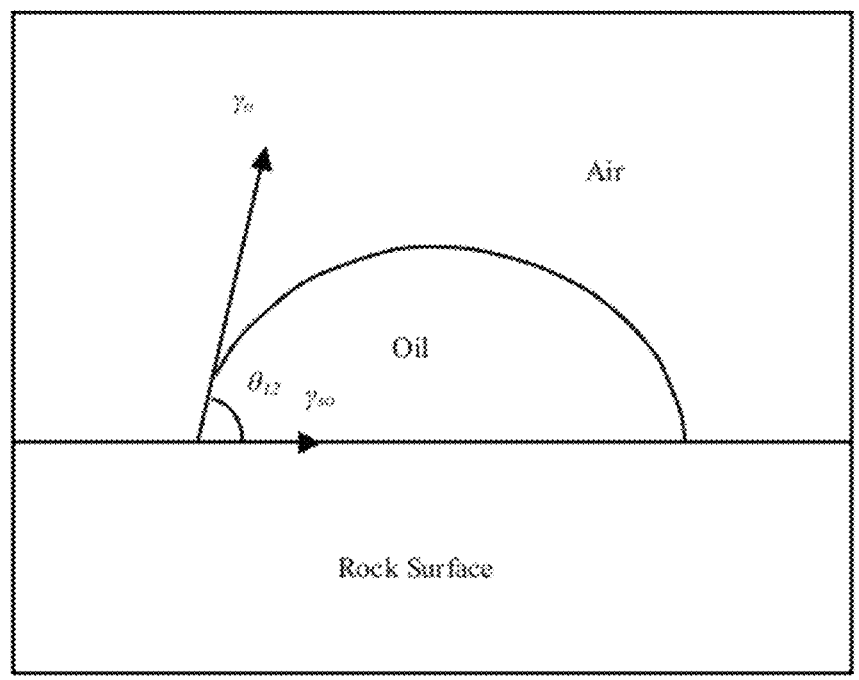
FIG. 4C shows a representation of young's equation with respect to an air/oil/rock surface system, according to an embodiment herein.

FIG. 4A-4C shows a representation of Young's Equation with respect to different Rock-Fluids systems. FIG. 4A shows a representation of young's equation with respect to an oil/water/rock surface system, according to an embodiment herein. With respect to FIG. 4A, $\gamma_{wo}$ is a interfacial tension between water and oil. $\gamma_{sw}$ is a surface tension between rock and water. $\gamma_{so}$ is a surface tension between rock and oil. The tensions $\gamma_{wo}$ and $\gamma_{sw}$ are making an angle of $\theta_{12}$. The Young equation for liquid/liquid/rock systems i.e. oil/water/rock system according to FIG. 4A can be described as:

$$\gamma_{ow} \cos\theta = \gamma_{os} - \gamma_{ws} \quad (2)$$

FIG. 4B shows are presentation of young's equation with respect to an air/water/rock surface system, according to an embodiment herein. With respect to FIG. 4B, $\gamma_w$ is a surface tension between water and air. $\gamma_{sw}$ is a surface tension between rock and water. The tensions $\gamma_w$ and $\gamma_{sw}$ are making an angle of $\theta_{12}$.

FIG. 4C shows a representation of young's equation with respect to an air/oil/rock surface system, according to an embodiment herein. With respect to FIG. 4C, $\gamma_o$ is a surface tension between oil and air. $\gamma_{so}$ is a surface tension between rock and oil. The tensions $\gamma_o$ and $\gamma_{so}$ are making an angle of $\theta_{12}$. Evaluating the $\gamma_{sw}$ and $\gamma_{so}$ from the FIGS. 4B and 4C, and substituting in Equation 2, results in, $$\cos\theta_{wo} = \frac{(\gamma_o \cos\theta_o) - (\gamma_w \cos\theta_w)}{\gamma_{wo}} \quad (3)$$

Now, rearranging Washburn equation, the Equation (1), to factor out $\gamma_{LV}$ (liquid-vapor surface tension) to get:

$$\gamma_{LV} = \frac{\mu}{C \cdot \rho^2 \cdot \cos\theta} \cdot \frac{m^2}{t} \quad (4)$$

Realizing that $\gamma_{LV}$ (liquid-vapor surface tension) is equivalent to $\gamma_o$ (oil-air surface tension) or $\gamma_w$ (water-air surface tension), and by substituting the equation (4) in equation (3) and cancelling out similar terms results in equation (5)

$$\cos\theta_{wo} = \frac{\left(\frac{m^2 \cdot \mu_o}{C\rho_o^2 t}\right) - \left(\frac{m^2 \cdot \mu_w}{C\rho_w^2 t}\right)}{\gamma_{wo}} \quad (5)$$

Figure 5:
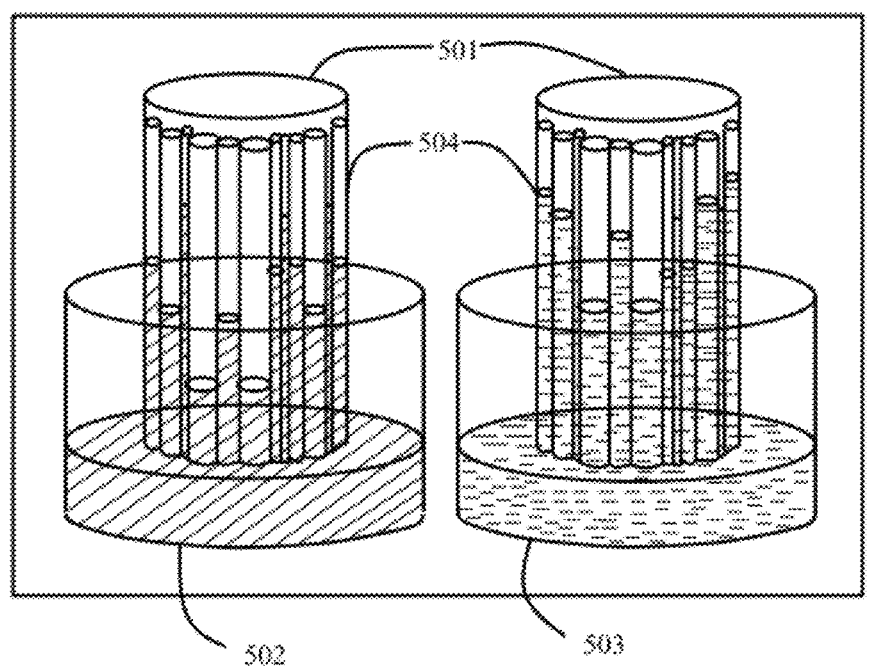
FIG. 5 shows imbibition of water and oil into air filled rock samples, according to an embodiment herein.

FIG. 5 shows imbibition of water and oil into air filled rock samples, according to an embodiment herein. With respect to FIG. 5, the rock samples 501 are inserted into water 502 and oil 503 separately for imbibition process to take place. The rock sample 501 is made up of a porous media. After some period of time, the water 502 and the oil 503 rises into the capillary tubes 504 present inside the rock samples 501 due to the capillary forces. The air behaves as a strong non-wetting phase in both the oil/air/solid and water/air/solid systems, which in turn shows that both oil and water behave as strong wetting phases. This results in equal air/oil and air/water capillary forces in the same porous media. So, for certain pore size distribution, the water imbibition is the same as that of oil imbibition because water or oil penetration in the porous media at any time is a function of the balance between gravity and capillary forces. This means that the heavier water penetrates into a less height for the same rock porosity and open area to flow than that of oil, less in volume but equal mass penetration. With respect to the FIG. 5, it is observed that for the core samples of the same rock type and dimensions, and for equal capillary forces, the mass of water imbibed into the core sample is approximately equal to the mass of oil imbibed in the core sample. So, $$\rho_w g V_w = \rho_o g V_o$$

Cancelling out g, we get, $\rho_w V_w = \rho_o V_o$

This implies that, $$m_w = m_o \qquad (6)$$

This allows to assume that m in the two terms at the numerator of equation (5) are equal, which allows to factor out the term $C \cdot m^2/t$ from the two terms, and resulting in, $$\cos\theta_{12} = \frac{(\mu_1 \cdot \rho_2^2) - (\mu_2 \cdot \rho_1^2)}{\rho_1^2 \rho_2^2 \cdot C \cdot \gamma_{L2L1}} \cdot \frac{m^2}{t} \qquad (7)$$

Equation (7) implies that after determining C, the constant of the porous media, the water/oil imbibition experiment are conducted and the contact angle θ, (the wettability), is directly determined for the oil/water/porous system.

In order to determine the constant C of the Washburn equation, the RIC experiment is first performed with n-dodecane/air/rock system. During this RIC experiment, n-dodecane imbibes into one of the core samples. A typical imbibition curve is observed.

Figure 6:
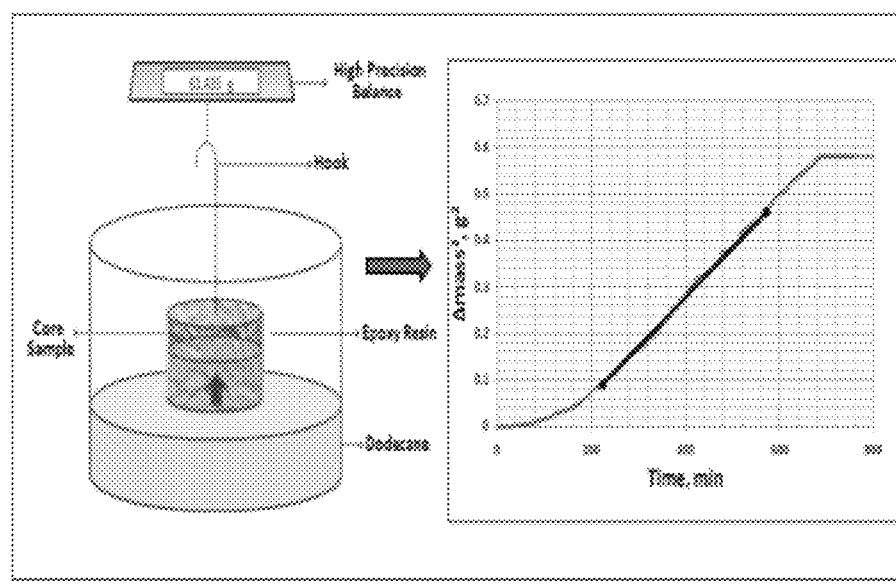
FIG. 6 shows a Rise in Core Experiment for Dodecane/Air/Rock System and an imbibition curve obtained after the dodecane solvent penetrates into the pores of the core samples, according to an embodiment herein.

FIG. 6 shows a Rise in Core Experiment for Dodecane/Air/Rock System and an imbibition curve obtained after the dodecane solvent penetrates in the pores of the core samples, according to an embodiment herein. With respect to FIG. 6, the core sample is connected to a high precision balance using a hook and a thread. The core sample is kept such that the bottom layer of the core sample just touches the dodecane solvent. The imbibition process was allowed to take place and a curve was obtained. Dodecane is an alkane that has very low surface energy making it to be very strongly wetting the rock sample in the presence of air, with contact angle, θ, equals to zero.

Having the value of the contact angle for this system, and the values the properties of n-dodecane (ρ, μ and γ), the constant C, is attained from equation (1), which is rearranged from equation (8).

$$C = \frac{\mu}{\gamma_{LV} \cdot \rho^2 \cdot \cos\theta} \cdot \frac{m^2}{t} \qquad (8)$$

According to the embodiment herein, the constant, C, is a characteristic of the porous material used to perform the experiments or the material to be analyzed. In the embodiments herein, C is determined for one of the core samples and utilized as the constant for neighboring core samples.

The second step of the RIC experimental process is to saturate a neighboring core sample with crude oil and subject the sample for the water imbibition formation. Then, by applying the slope of the RIC curve, $m^2/t$, fluid properties of the oil/brine system (ρ, μ of both crude oil and formation water as well as interfacial tension, γ), and the C value determined from the neighboring core sample into Equation (7) to calculate the contact angle θ.

Experimental Data

The technique was applied on Berea core samples with different wettability. The RIC repeatedly predicted the cores' wettability. Furthermore, and for the sake of assurance, RIC wettability measurements were compared to the ambient conditions of modified Amott-USBM measurements for a thick limestone oil reservoir using core plug pairs from different heights above the free water level. The results compared well. The RIC technique proved to be much simpler to construct, much faster to perform and much easier to analyze and interpret than traditional methods.

Example 1

Demonstration of the RIC Concept

Berea sandstone core samples, synthetic brine and kerosene were used to prove the RIC concept. For the past 30 years, Berea sandstone core samples have been widely recognized by the petroleum industry as the best outcrop rock for laboratory testing. To demonstrate the RIC concept, this section presents the series of measurements performed on core plugs cut from a core sample of 19.62% porosity and 162 md permeability.

Figure 7:
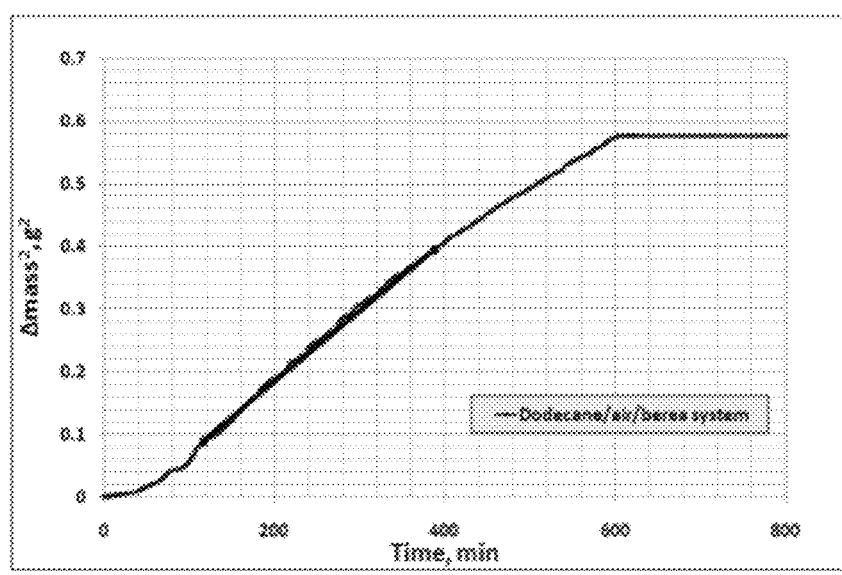
FIG. 7 shows RIC imbibition curve for n-dodecane/air system for one of the core samples imbibed, according to an embodiment herein.

FIG. 7 shows RIC imbibition curve for n-dodecane/air/rock system for one of the core samples, according to an embodiment herein. With respect to FIG. 7, a mass change vs. time data of dodecane imbibition into the core plug was recorded to obtain a curve. Then using the curve obtained in FIG. 7, the slope, $m^2/t$ of the curve was determined. The slope came out to be 0.0010657 $g^2$/min or $1.7761 \times 10^{-5}$ $g^2$/sec. Then using the properties of the air and dodecane, the slope value was applied in Equation (8) to determine value of C, in the following way:

$$C = \frac{1.493 cp \left(0.01 \cdot \frac{\text{dyne} \cdot s}{\text{cm}^2} \cdot \frac{1}{cp}\right)}{0.748^2 \left(\frac{g}{\text{cm}^3}\right) \cdot 25.35 \left(\frac{\text{dyne}}{\text{cm}}\right) \cdot \cos 0} \cdot (0.0010657) \left(\frac{g^2}{\text{min}} \cdot \frac{\text{min}}{60 \text{ sec}}\right) \qquad (8)$$

$C = 1.869724 \cdot 10^{12} \, \mu m^5$

Thus the C came out to be $1.869724 \cdot 10^{12} \, \mu m^5$.

Figure 8:
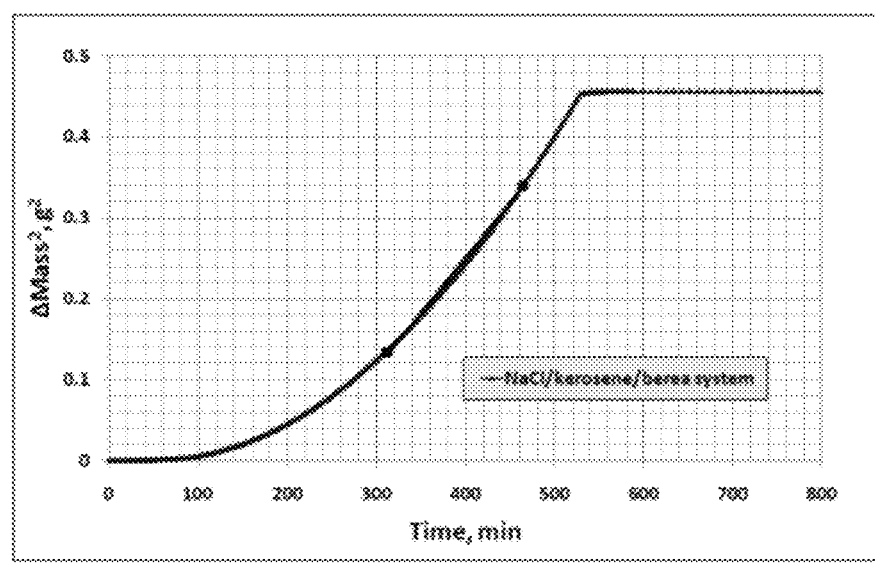
FIG. 8 shows a rise in core results for Brine/Kerosene/Berea System, according to an embodiment herein.

After calculating constant C for a selected rock sample, a neighboring core plug was saturated by 100% oil (kerosene). FIG. 8 presents RIC imbibition curve for Kerosene/water/rock of this neighboring core sample, according to an embodiment herein. With respect to FIG. 8, the mass change vs time data of water imbibition into the core plug was recorded. The slope, $m^2/t$ of the linear part was determined. The slope of the linear part of the imbibition curve came out to be 0.00128 $g^2$/min.

Substituting the value of this slope in Equation (7) and using the measured physical properties of both the brine and the kerosene, gave:

$$\cos\theta_{wo} = \frac{\left(1.24 cp \cdot (1.17)^2 \left(\frac{g}{\text{cm}^3}\right)\right) - \left(1.1203 cp \cdot (0.804)^2 \left(\frac{g}{\text{cm}^3}\right)\right)}{(0.804)^2 \left(\frac{g}{\text{cm}^3}\right) \cdot (1.17)^2 \left(\frac{g}{\text{cm}^3}\right) \cdot 29.35 \left(\frac{\text{dyn}}{\text{cm}}\right) \cdot C(\text{cm}^5)} \cdot \frac{m^2}{t} \left(\frac{g^2}{\text{min}}\right)$$

$\cos\theta_{wo} =$ $$\frac{\left(1.24 cp \left(0.01 \cdot \frac{\text{dyne} \cdot s}{\text{cm}^2} \cdot \frac{1}{cp}\right) \cdot (1.17)^2 \left(\frac{g}{\text{cm}^3}\right)\right) -}{(0.804)^2 \left(\frac{g}{\text{cm}^3}\right) \cdot (1.17)^2 \left(\frac{g}{\text{cm}^3}\right) \cdot 29.35 \left(\frac{\text{dyn}}{\text{cm}}\right) \cdot C(\text{cm}^5)}$$

$$\frac{\left(1.1203 cp \left(0.01 \cdot \frac{\text{dyne} \cdot s}{\text{cm}^2} \cdot \frac{1}{cp}\right) \cdot (0.804)^2 \left(\frac{g}{\text{cm}^3}\right)\right)}{(0.804)^2 \left(\frac{g}{\text{cm}^3}\right) \cdot (1.17)^2 \left(\frac{g}{\text{cm}^3}\right) \cdot 29.35 \left(\frac{\text{dyn}}{\text{cm}}\right) \cdot C(\text{cm}^5)} \cdot \frac{m^2}{t} \left(\frac{g^2}{\text{min}} \cdot \frac{\text{min}}{60 \text{ sec}}\right)$$

-continued $$\cos\theta_{wo} = \frac{(0.016974) - (0.007241)}{(25.9711) \cdot C} \cdot (2.133 \cdot 10^{-5})$$

$$\cos\theta_{wo} = \frac{(0.016974) - (0.007241)}{(25.9711) \cdot (1.87 \cdot 10^{-8})} \cdot (2.133 \cdot 10^{-5})$$

$$\cos\theta_{wo} = 0.427$$

then $\theta_{wo} = 64.69$

Figure 9:
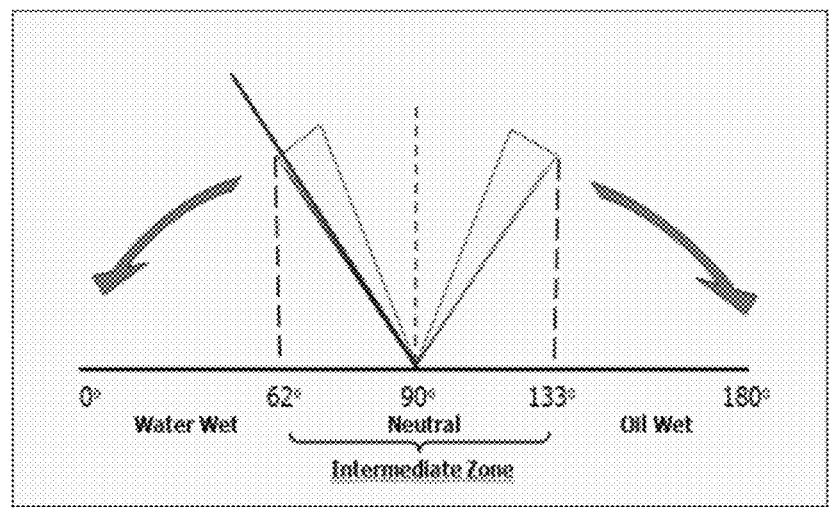
FIG. 9 shows wettability spectra for the Brine/Kerosene/Berea System, according to an embodiment herein.

Thus the contact angle $\theta_{wo}$ was obtained as 64.69°. This angle is represented in FIG. 9. FIG. 9 shows wettability spectra for the Brine/Kerosene/Berea System showing the contact angle, according to an embodiment herein. With Respect to FIG. 9, the contact angle $\theta_{wo}$ is 64.69°. A spectra ranging from a completely water wet (at 0°) to completely oil wet (at 180°) can be observed. An intermediate zone ranging from 62° to 133° can be seen depicting a weakly water wet to weakly oil wet. At 90° the sample is neutral in terms of water wettability and oil wettability. The black line shows the contact angle obtained, $\theta_{wo}$, 64.69°, for the core plug sample with the brine/kerosene/Berea system. With respect to the FIG. 9, it was concluded that the wettability of the natural Berea sandstone core sample was weakly water wet.

Example 2

Repeatability Analysis

To prove that the RIC experiment systematically repeatedly produces the same results, the RIC experiments were repeatedly performed on the same rock-fluid system. It should produce consistent and similar results for all the samples.

Figure 10:
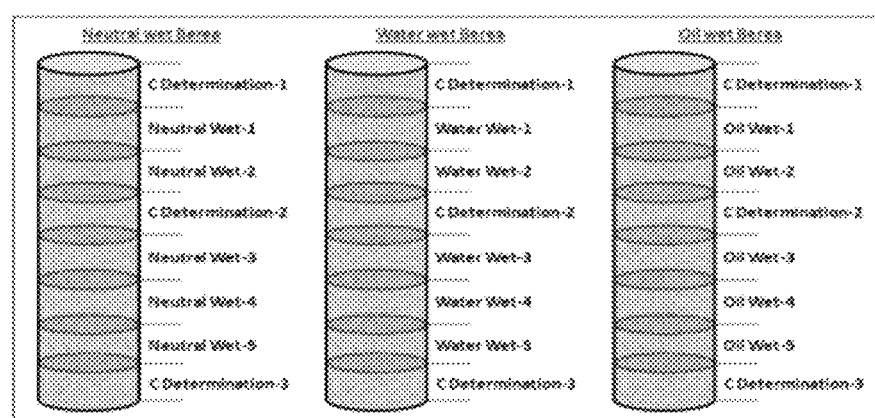
FIG. 10 shows the Core Selection for RIC Repeatability Experiments, according to an embodiment herein.

A natural Berea core sample of 1.5 inches diameter and 12 cm length was used for this purpose. The core sample was cut into eight smaller core plugs of 1.5 inches diameter and 1.5 cm long each. FIG. 10 shows the core Selection for RIC Repeatability Experiments, according to an embodiment herein. With respect to FIG. 10, three of the core plugs were used for the determination of C and five were used for the wettability determination. To prove the repeatability and considering rock heterogeneity, C values and the wettability values should be very consistent and close to each other. The top, middle and bottom core plugs were chosen for the C determination experiments. Other core plugs were utilized for the RIC wettability experiments of brine/kerosene/Berea rock system.

Figure 11:
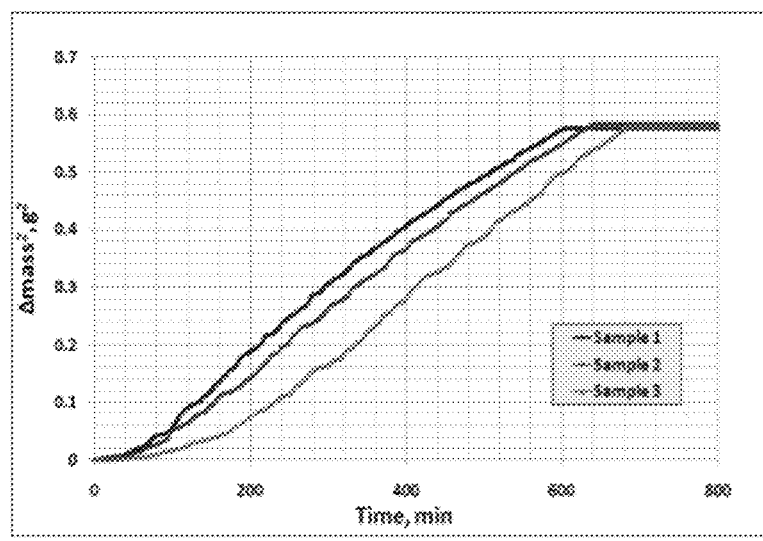
FIG. 11 shows an imbibition curve for three different samples of Dodecane/Air/Natural Berea system for the RIC Repeatability experiments, according to an embodiment herein.

Three samples were imbibed with dodecane solvent for the determination of C, as dodecane/Air/Natural Berea system. FIG. 11 shows an imbibition curve for three different samples of dodecane/Air/Natural Berea system for the RIC Repeatability experiments, according to an embodiment herein. With respect to FIG. 11, the tendencies of three different dodecane/air/Berea rock system measurements have a good correlation with very close slopes. Using the curves in FIG. 11, slopes for the three different samples were calculated. The constant C was also calculated by the process according to EXAMPLE 1 herein. Table 1 shows the slope of the three imbibition curves presented in FIG. 11. The table also shows the calculated C values for the Berea core plugs.

TABLE 1

Average Slope and Calculated C Values of 3 adjacent Core Samples

| Sample # | Average Slope | Average C value |
|---|---|---|
| 1 | 0.001018323 | $1.786540 \cdot 10^{12}$ |
| 2 | 0.001030407 | $1.807741 \cdot 10^{12}$ |
| 3 | 0.000984014 | $1.726349 \cdot 10^{12}$ |

For perfectly similar porous material of the three core plugs, and for ideal experiments with no measurement error and no uncertainty involved, the C values should be exactly the same. However, these are real experiments with some associated uncertainty in picking up the slopes of the curves, which results in some differences in the C values. Furthermore, these little differences in the C values, reflect the differences in the nature of porous media of the three core plugs used for C determination. The C value used for the determination of the wettability of the rest of the core plugs is the average value of the three values derived for C as mentioned in Table 1. The average C value came out to be $C = 1.7735433 \times 10^{12}$ $\mu m^5$.

Figure 12:
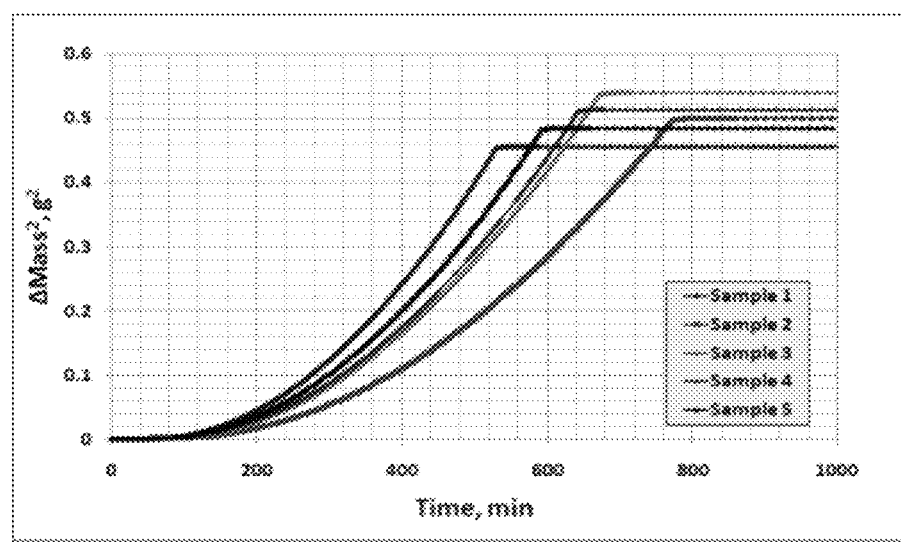
FIG. 12 shows imbibition curve for five adjacent core samples using Brine/Kerosene/Berea rock system, according to an embodiment herein.

The RIC experiments were then performed on the adjacent five core samples using the Brine/Kerosene/Berea rock system. The imbibition curves were obtained for the five core samples with Brine/Kerosene/Berea rock system. FIG. 12 shows imbibition curves for five adjacent core samples using Brine/Kerosene/Berea rock system, according to an embodiment herein. Slopes were calculated using the curve obtained in FIG. 12. The contact angles were also calculated. Table 2 shows the slope of the five imbibition curves presented in FIG. 12. The table also shows the calculated contact angles for the Berea core plugs using average C value.

TABLE 2

Average Slope and Calculated Contact Angles for five core samples

| Sample # | Slope, $m^2/t$ | $\theta$ |
|---|---|---|
| 1 | 0.001188239 | 65.38 |
| 2 | 0.000966096 | 70.20 |
| 3 | 0.001206837 | 64.97 |
| 4 | 0.001199857 | 65.12 |
| 5 | 0.001258797 | 63.81 |

For perfectly similar porous material of the five core plugs, and for ideal experiments with no measurement error and no uncertainty involved, the contact angles should be exactly the same. However, these are real experiments with some associated uncertainty in picking up the slopes of the curves, which is going to induce some differences in the contact angle values. Furthermore, these little differences in the contact angles reflect the differences in the nature of porous media of the five core plugs used for this purpose.

Figure 13:
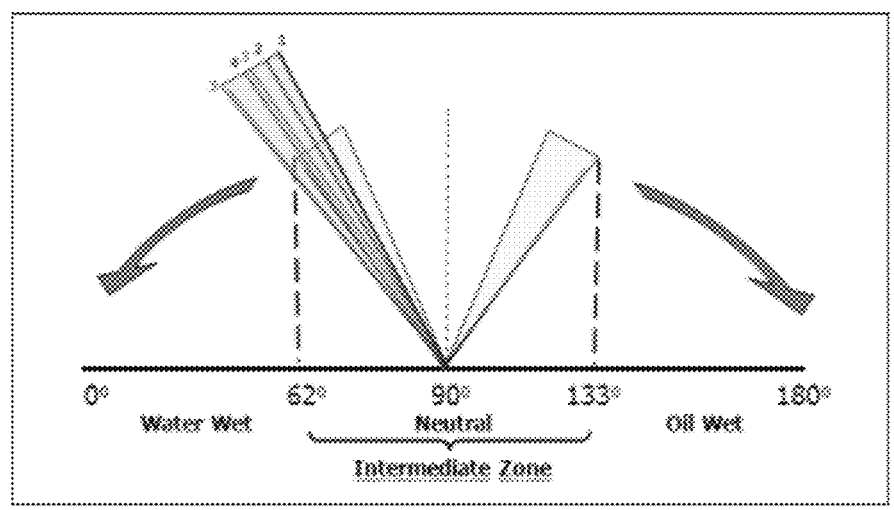
FIG. 13 shows a wettability envelop of the natural berea five rock samples or core plug, according to an embodiment herein.

FIG. 13 shows a wettability envelop of the natural Berea five rock samples or core plug, according to an embodiment herein. With respect to FIG. 13, it can be observed that the wettability of all the five core samples is very close and shows repeated results. The contact angles of all five core plugs shows that the natural Berea rock is weakly water wet. It is clear that the RIC experiment is repeatable confirming that the concept and the experiment are not randomly producing the wettability results.

Example 3

Analysis of Uncertainty

In this section, possible uncertainties are considered to determine their effect on the calculated wettability. Two uncertainties are involved including picking up the slope of the imbibition curves for both RIC-C determination and RIC-wettability experiments. Table 3 shows the results of the uncertainty analysis performed on picking up the slope of the Dodecane/Air/Berea rock system including minimum and maximum slopes as well as eight random trials. The table also shows the effect of this uncertainty on the determination of the C values.

TABLE 3

Uncertainty Analysis of dodecane/Air/Naturally Wet Berea System

|  | Sample 1 | Sample 2 | Sample 3 |
|---|---|---|---|
| Minimum slope (g²/min) | 0.0009106 | 0.0008884 | 0.0007928 |
| Maximum slope | 0.0011776 | 0.0011080 | 0.0010739 |
| Random slope_1 | 0.0010657 | 0.0010655 | 0.0010649 |
| Random slope_2 | 0.0010459 | 0.0010454 | 0.0010045 |
| Random slope_3 | 0.0010160 | 0.0010386 | 0.0009827 |
| Random slope_4 | 0.0010190 | 0.0009172 | 0.0008612 |
| Random slope_5 | 0.0010340 | 0.0010737 | 0.0009728 |
| Random slope_6 | 0.0010152 | 0.0010421 | 0.0010065 |
| Random slope_7 | 0.0009631 | 0.0010595 | 0.0010739 |
| Random slope_8 | 0.0009356 | 0.0010652 | 0.0010064 |
| Average Slope | 0.0010183 | 0.0010304 | 0.0009840 |
| C_min, μm⁵ | $1.697564 \cdot 10^{12}$ | $1.558757 \cdot 10^{12}$ | $1.390928 \cdot 10^{12}$ |
| C_max | $2.066066 \cdot 10^{12}$ | $1.943976 \cdot 10^{12}$ | $1.884096 \cdot 10^{12}$ |
| C_Random_1 | $1.869724 \cdot 10^{12}$ | $1.869408 \cdot 10^{12}$ | $1.868417 \cdot 10^{12}$ |
| C_Random_2 | $1.835075 \cdot 10^{12}$ | $1.834110 \cdot 10^{12}$ | $1.762348 \cdot 10^{12}$ |
| C_Random_3 | $1.782496 \cdot 10^{12}$ | $1.822196 \cdot 10^{12}$ | $1.724173 \cdot 10^{12}$ |
| C_Random_4 | $1.787850 \cdot 10^{12}$ | $1.609166 \cdot 10^{12}$ | $1.511015 \cdot 10^{12}$ |
| C_Random_5 | $1.814062 \cdot 10^{12}$ | $1.883782 \cdot 10^{12}$ | $1.706751 \cdot 10^{12}$ |
| C_Random_6 | $1.781228 \cdot 10^{12}$ | $1.828303 \cdot 10^{12}$ | $1.765965 \cdot 10^{12}$ |
| C_Random_7 | $1.689768 \cdot 10^{12}$ | $1.858882 \cdot 10^{12}$ | $1.884096 \cdot 10^{12}$ |
| C_Random_8 | $1.641571 \cdot 10^{12}$ | $1.868825 \cdot 10^{12}$ | $1.765706 \cdot 10^{12}$ |
| Average C constant | $1.786540 \cdot 10^{12}$ | $1.807741 \cdot 10^{12}$ | $1.726349 \cdot 10^{12}$ |

From the table 3, it can be seen that the slopes are still very close to each other and when compared to the average value of all. The same conclusion could be made about the C values. This could be easily noted by comparing the most of the minimum and maximum possible C values as well as the average one.

The uncertainty analysis was taken a step further by checking the effect of the C values on the contact angles of the five core plugs of this set of experiments and is presented in Table 4. Table 4 also includes the uncertainty involved in picking the slope of the RIC wettability curves.

TABLE 4

Variation in the determined Contact Angle of the five core samples due to uncertainties in the slopes of the imbibition curves and variation in the C values (considering the minimum, maximum and average values of slopes and C values)

|  | C min | C max | C avg |
|---|---|---|---|
| Sample 1 | | | |
| Min. Slope | 65.11 | 71.07 | 69.03 |
| Max. slope | 58.25 | 66.06 | 63.42 |
| Avg. Slope | 60.66 | 67.80 | 65.38 |
| Sample 2 | | | |
| Min. Slope | 69.39 | 74.25 | 72.58 |
| Max. slope | 64.09 | 70.31 | 68.19 |
| Avg. Slope | 66.52 | 72.11 | 70.20 |
| Sample 3 | | | |
| Min. Slope | 62.65 | 69.25 | 67.00 |
| Max. slope | 58.75 | 66.43 | 63.83 |
| Avg. Slope | 60.16 | 67.44 | 64.97 |

TABLE 4-continued

Variation in the determined Contact Angle of the five core samples due to uncertainties in the slopes of the imbibition curves and variation in the C values (considering the minimum, maximum and average values of slopes and C values)

|  | C min | C max | C avg |
|---|---|---|---|
| Sample 4 | | | |
| Min. Slope | 61.90 | 68.70 | 66.39 |
| Max. slope | 58.31 | 66.11 | 63.47 |
| Avg. Slope | 60.35 | 67.58 | 65.12 |
| Sample 5 | | | |
| Min. Slope | 62.46 | 69.11 | 66.84 |
| Max. slope | 56.59 | 64.88 | 62.08 |
| Avg. Slope | 58.73 | 66.41 | 63.81 |

With respect to Table-4, considering the extreme values of the C values as well as the extreme values of the RIC slopes, the contact angles for each core plug stayed very close. This shows that any uncertainty involved in this work should not affect the final wettability result for any core plug.

Application of the RIC with Other Ranges of Wettability

Example 4

Water Wet Core Samples

The embodiments herein provide a method of characterization that works for all ranges of wettability. Berea core samples were treated to make them more water wet. Dry weights ($W_1$) of the core samples were measured after permeability and porosity determination. Then, core samples were cleaned by using toluene in a soxhlet for 3 days. Following the cleaning procedure, another measurement of weight ($W_2$) was recorded and core samples were taken to an oven in 110° C. until the subsequent mass change approached zero. Thus, core samples were prepared to have more water wet behavior. Just as before, core plug was divided into eight core samples. Three were used for C determination and the other five were used for wettability measurement.

Figure 14:
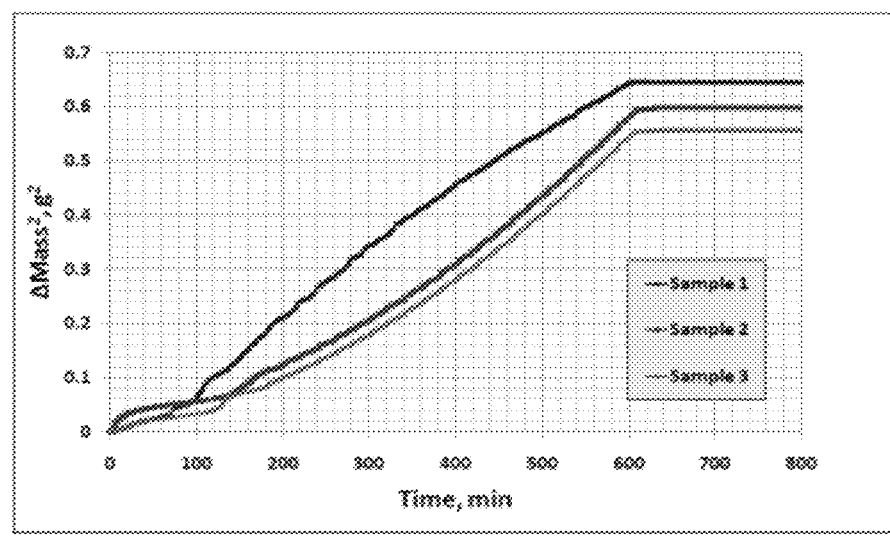
FIG. 14 shows the RIC imbibition curves for three different samples of Dodecane/Air/Water Wet Berea system for determination of C, according to an embodiment herein.

FIG. 14 shows the RIC imbibition curves for three different samples of Dodecane/Air/Water Wet Berea system for determination of C, according to an embodiment herein. With respect to FIG. 14, the slopes for all the three samples showed repeatability. RIC experiments were performed on the adjacent five core samples using Brine/Kerosene/Berea rock system.

Figure 15:
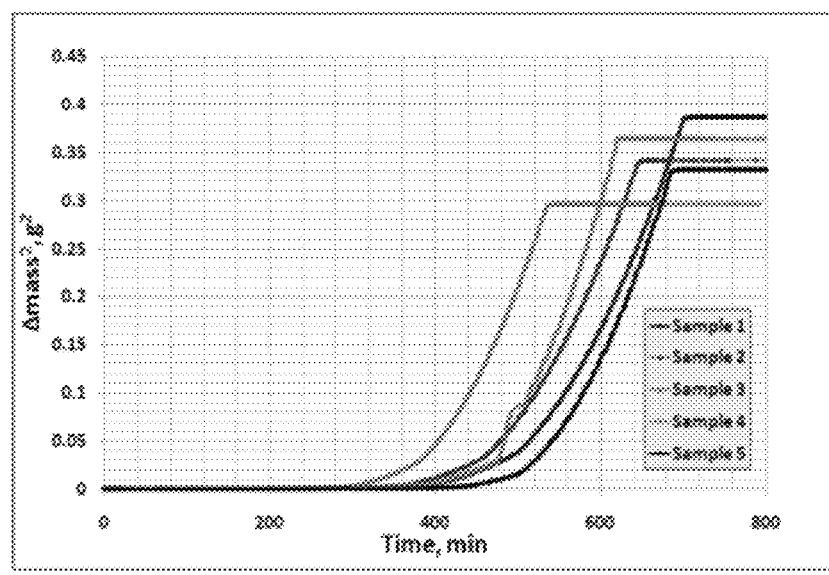
FIG. 15 shows the RIC imbibition curves for five different samples of Kerosene/Brine/Water Wet Berea, according to an embodiment herein.

FIG. 15 shows the RIC imbibition curves for five different samples of Kerosene/Brine/Water Wet Berea, according to an embodiment herein. With respect to FIG. 15, it was observed that the slopes for all the five samples showed repeatability. The contact angles were calculated.

Figure 16:
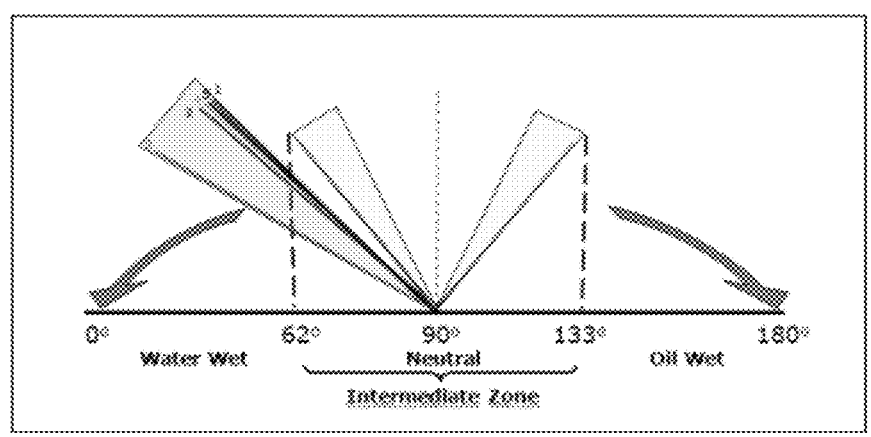
FIG. 16 shows the wettability envelope of the five core plugs samples, according to an embodiment herein.

FIG. 16 shows the wettability envelope of the five core plug samples, according to an embodiment herein. With respect to FIG. 16, it is clear that the RIC experiment is repeatable confirming that the concept and the experiment are not randomly producing the wettability results.

The uncertainty analysis was done. Table 5 shows the uncertainty in the slope of the RIC imbibition curves and their effect on the calculation of the C Constant. The table also shows the effect of this uncertainty on the determination of the C values. The uncertainty analysis was performed by picking up the slope of the Dodecane/Air/Berea rock system including minimum and maximum slopes as well as 8 random trials.

TABLE 5

Uncertainty in the slope of the RIC imbibition curves and their effect on the calculation of the C Constant.

|  | Sample 1 | Sample 2 | Sample 3 |
|---|---|---|---|
| Min. Slope | 0.0011130 | 0.0009980 | 0.0009680 |
| Max. Slope | 0.0011950 | 0.0010900 | 0.0010820 |
| Random Slope_1 | 0.0011560 | 0.0010340 | 0.0010110 |
| Random Slope_2 | 0.0011220 | 0.0010630 | 0.0010310 |
| Random Slope_3 | 0.0011480 | 0.0010810 | 0.0009700 |
| Random Slope_4 | 0.0011950 | 0.0010440 | 0.0010560 |
| Random Slope_5 | 0.0011390 | 0.0010490 | 0.0010430 |
| Random slope_6 | 0.0011390 | 0.0009910 | 0.0010040 |
| Random Slope_7 | 0.0011360 | 0.0010290 | 0.0010410 |
| Random Slope_8 | 0.0011490 | 0.0010390 | 0.0010260 |
| C_min | $1.954533.10^{12}$ | $1.732572.10^{12}$ | $1.683244.10^{12}$ |
| C_max | $2.083460.10^{12}$ | $1.750213.10^{12}$ | $1.889324.10^{12}$ |
| C_Random_1 | $2.016675.10^{12}$ | $1.900176.10^{12}$ | $1.766653.10^{12}$ |
| C_Random_2 | $1.966517.10^{12}$ | $1.801292.10^{12}$ | $1.803221.10^{12}$ |
| C_Random_3 | $2.016460.10^{12}$ | $1.856821.10^{12}$ | $1.773211.10^{12}$ |
| C_Random_4 | $2.083680.10^{12}$ | $1.883212.10^{12}$ | $1.773211.10^{12}$ |
| C_Random_5 | $1.986417.10^{12}$ | $1.816672.10^{12}$ | $1.816653.10^{12}$ |
| C_Random_6 | $1.986325.10^{12}$ | $1.850982.10^{12}$ | $1.754434.10^{12}$ |
| C_Random_7 | $1.983632.10^{12}$ | $1.733242.10^{12}$ | $1.816610.10^{12}$ |
| C_Random_8 | $2.016684.10^{12}$ | $1.803321.10^{12}$ | $1.833654.10^{12}$ |
| Average C Constant | $2.009412.10^{12}$ | $1.812850.10^{12}$ | $1.798912.10^{12}$ |

From the table 5, it can be seen that the slopes are still very close to each other and when compared to the average value of all. The same conclusion could be made about these C values. This could be easily noted by comparing the most minimum and maximum possible C values as well as the average one.

The contact angles for the five samples were calculated. Table 6 shows the variation of the contact angles of the five samples as results of the uncertainty of the constant C and the evaluation of the RIC imbibition slope.

TABLE 6

Variation of the contact angles of the five samples as a result of the uncertainty of the constant C and the evaluation of the RIC imbibition slope

|  | C min | C max | C avg |
|---|---|---|---|
| Sample 1 | | | |
| Min. Slope | 50.11 | 54.05 | 52.19 |
| Max. slope | 46.99 | 51.37 | 49.31 |
| Avg. Slope | 53.77 | 57.25 | 55.61 |
| Sample 2 | | | |
| Min. Slope | 54.3 | 57.72 | 56.1 |
| Max. slope | 47.41 | 51.73 | 49.7 |
| Avg. Slope | 51.16 | 54.97 | 53.17 |
| Sample 3 | | | |
| Min. Slope | 39.61 | 45.16 | 42.59 |
| Max. slope | 24.24 | 33.43 | 29.37 |
| Avg. Slope | 33.39 | 40.16 | 37.06 |
| Sample 4 | | | |
| Min. Slope | 55.61 | 58.87 | 57.32 |
| Max. slope | 50.2 | 54.14 | 52.28 |
| Avg. Slope | 52.21 | 55.88 | 54.15 |
| Sample 5 | | | |
| Min. Slope | 59.27 | 62.12 | 60.77 |
| Max. slope | 47.52 | 51.82 | 49.8 |
| Avg. Slope | 58.73 | 56.71 | 55.21 |

From table 6, it is clear that the variations of the contact angles are within a reasonable value. None of the variations were to the point of changing the possible wettability of the core sample from one wettability band to another.

Example 5

Oil Wet Core Samples

Berea core samples were treated to make them more oil wet. Air particles inside the sample were taken by using the vacuum desiccators. The sample was 100% saturated with crude oil for 48 hours. Then, the samples were taken to the oven for drying process. Drying process was continued in 110° C. until the mass change of each sample was close or equal to zero. The precipitation of heavy oil components on the surface of the rock minerals made it more oil wet. Core plug was divided into eight core samples. Three of them were used for C determination and the other five were used for wettability measurement.

Figure 17:
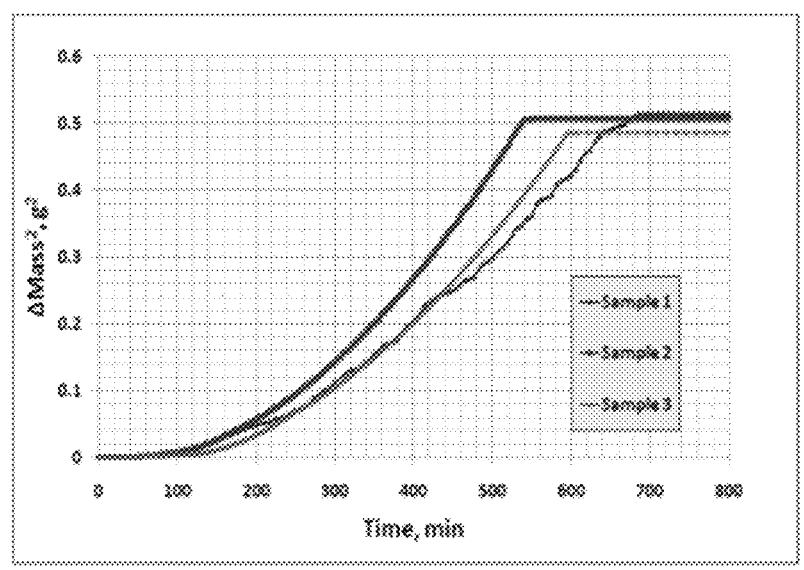
FIG. 17 shows the RIC imbibition curve showing the RIC repeatability results for three different samples of Dodecane/Air/Oil Wet Berea system for determination of C, according to an embodiment herein.

FIG. 17 shows the RIC imbibition curve showing the RIC repeatability results for three different samples of Dodecane/Air/Oil Wet Berea system for determination of C, according to an embodiment herein. With respect to FIG. 17, the imbibition curves for the three samples show a similarity. RIC experiments were performed on the adjacent five core samples using Brine/Kerosene/Berea rock system.

Figure 18:
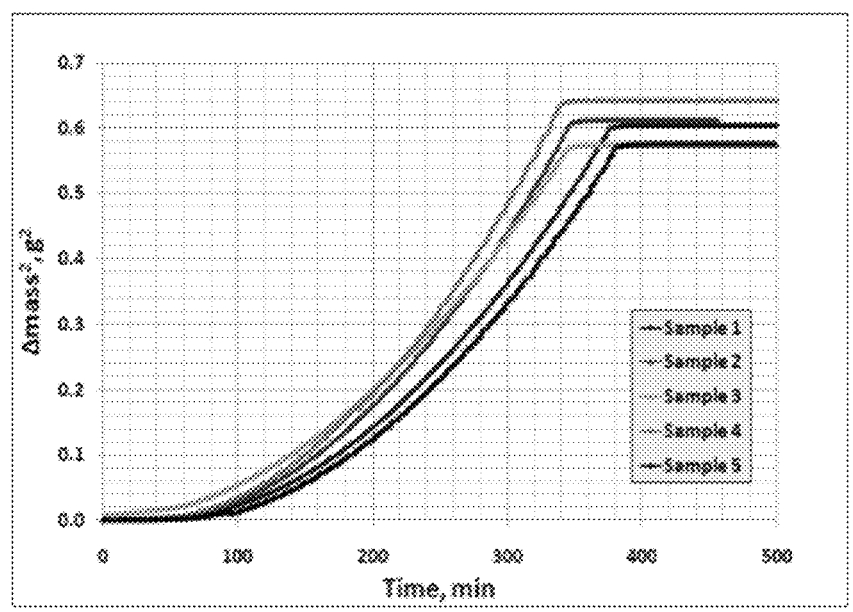
FIG. 18 shows the RIC imbibition curves showing the RIC repeatability results for five different samples of Kerosene/brine/oil wet Berea system, according to an embodiment herein.

FIG. 18 shows the RIC imbibition curves showing the RIC repeatability result as for five different samples of Kerosene/brine/oil wet Berea system, according to an embodiment herein. With respect to FIG. 18, the imbibition curves for five adjacent samples showed similarity.

Figure 19:
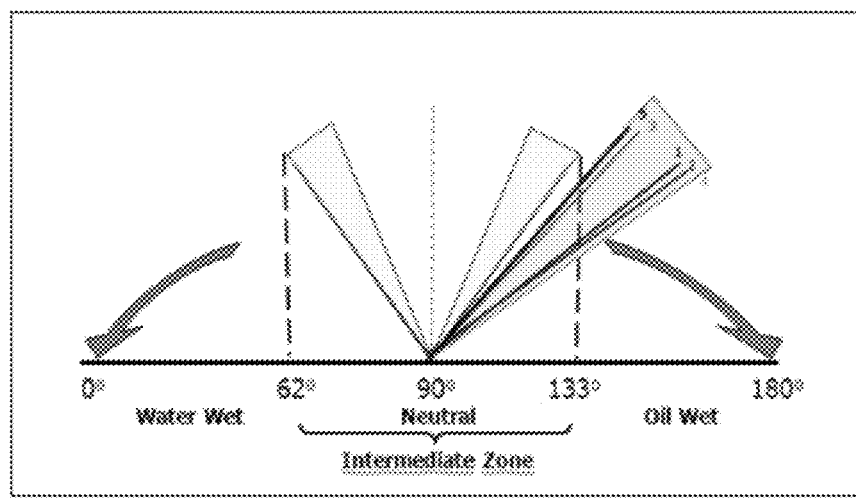
FIG. 19 shows the wettability envelope of the five core plugs samples, according to an embodiment herein.

FIG. 19 shows the wettability envelope of the five core plugs samples, according to an embodiment herein. With respect to FIG. 19, it is clear that the RIC experiment is repeatable confirming that the concept and the experiment are not randomly producing the wettability results.

Table 7 presents the uncertainty analysis performed on picking up the slope of the Dodecane/Air/Berea rock system including minimum and maximum slopes as well as 8 random trials.

TABLE 7

Uncertainty in the slope of the RIC imbibition curves and their effect on the calculation of the C Constant.

|  | Sample 1 | Sample 2 | Sample 3 |
|---|---|---|---|
| Min. Slope | 0.0009252 | 0.0008582 | 0.0010372 |
| Max. Slope | 0.0010755 | 0.0011053 | 0.0011586 |
| Random Slope_1 | 0.0010461 | 0.0009191 | 0.0011134 |
| Random Slope_2 | 0.0010082 | 0.0009305 | 0.0010696 |
| Random Slope_3 | 0.0009899 | 0.0010682 | 0.0011075 |
| Random Slope_4 | 0.0010333 | 0.0010363 | 0.0011394 |
| Random Slope_5 | 0.0010166 | 0.0009679 | 0.0010588 |
| Random Slope_6 | 0.0009887 | 0.0010727 | 0.0010749 |
| Random Slope_7 | 0.0010358 | 0.0009674 | 0.0011468 |
| Random slope_8 | 0.0009881 | 0.0011013 | 0.0011247 |
| Average Slope | 0.0010107 | 0.0010027 | 0.0011031 |
| C_min | $1.616574.10^{12}$ | $1.500129.10^{12}$ | $1.816588.10^{12}$ |
| C_max | $1.883641.10^{12}$ | $1.933182.10^{12}$ | $2.014391.10^{12}$ |
| C_Random_1 | $1.834112.10^{12}$ | $1.601292.10^{12}$ | $1.955421.10^{12}$ |
| C_Random_2 | $1.766455.10^{12}$ | $1.620918.10^{12}$ | $1.866344.10^{12}$ |
| C_Random_3 | $1.733347.10^{12}$ | $1.866623.10^{12}$ | $1.933486.10^{12}$ |
| C_Random_4 | $1.803451.10^{12}$ | $1.814372.10^{12}$ | $1.983346.10^{12}$ |
| C_Random_5 | $1.784125.10^{12}$ | $1.683243.10^{12}$ | $1.850211.10^{12}$ |
| C_Random_6 | $1.733471.10^{12}$ | $1.866332.10^{12}$ | $1.889112.10^{12}$ |
| C_Random_7 | $1.801245.10^{12}$ | $1.683331.10^{12}$ | $2.008432.10^{12}$ |
| C_Random_8 | $1.733411.10^{12}$ | $1.916577.10^{12}$ | $1.966785.10^{12}$ |
| Average C Constant | $1.768983.10^{12}$ | $1.748599.10^{12}$ | $1.928411.10^{12}$ |

Again, the results show that the slopes are still very close to each other and when compared to the average value of all. The table also shows the effect of this uncertainty on the determination of the C values. The same conclusion could be drawn about these C values. This could be easily noted by comparing the most minimum and maximum possible C values as well as the average one.

Table 8 presents the effect of variation in the C values as well as the slope of RIC imbibition curves on the determination of the wettability contact angles of the five samples.

TABLE 8

Variation of the contact angles of the five samples as results of the uncertainty of the constant C and the evaluation of the RIC imbibition slope

|  | C min | C max | C avg |
|---|---|---|---|
| Sample 1 | | | |
| Min. Slope | 154.3 | 139.68 | 144.92 |
| Max. slope | 173.84 | 147.27 | 154.55 |
| Avg. Slope | 157.88 | 141.61 | 147.28 |
| Sample 2 | | | |
| Min. Slope | 139.02 | 129.70 | 133.29 |
| Max. slope | 165.08 | 144.85 | 151.36 |
| Avg. Slope | 159.79 | 142.56 | 148.46 |
| Sample 3 | | | |
| Min. Slope | 144.00 | 133.20 | 137.29 |
| Max. slope | 152.49 | 138.63 | 143.66 |
| Avg. Slope | 146.50 | 134.88 | 139.24 |
| Sample 4 | | | |
| Min. Slope | 159.58 | 142.46 | 148.34 |
| Max. slope | 179.02 | 147.78 | 155.24 |
| Avg. Slope | 163.90 | 144.38 | 150.76 |
| Sample 5 | | | |
| Min. Slope | 141.94 | 131.78 | 135.66 |
| Max. slope | 149.11 | 136.56 | 141.21 |
| Avg. Slope | 146.26 | 134.72 | 139.05 |

The results indicate that the variations of the contact angles are within reason. None of the variations were to the point of changing the possible wettability of the core sample from one wettability band to another.

Example 6

Amott and the USBM are the most commonly utilized wettability testing methods in the petroleum industry. To compare the RIC method with the Amott and USBM techniques, twelve twinned core plugs pairs were taken from a freshly preserved limestone core taken from a thick, multilayer reservoir in a giant carbonate oil field. Table 9 presents the depth and permeability of the twin core plugs. In addition to the primary objective, these tests would provide a vertical wettability profile for the reservoir at the crestal location of the reservoir. Filtered reservoir dead crude oil was used for all tests. Synthetic formation water was mixed and deoxygenated using nitrogen.

TABLE 9

Depth and Permeability of Twin Core Samples

| | Amott & USBM Samples | | RIC Samples | |
|---|---|---|---|---|
| Formation | Depth, ft | Perm, md | Depth, ft | Perm, md |
| YZ1A | XX95.00 | 11 | XX94.80 | 65 |
| YZ1A | XX07.50 | 7 | XX07.30 | 19 |
| YZ1A | XX38.60 | 29 | XX38.40 | 25 |
| YZ2 | XX85.20 | 68 | XX85.75 | 41 |
| YZ2 | XX50.50 | 4 | XX50.30 | 13 |
| YZ2 | XX01.50 | 11 | XX02.00 | 28 |

TABLE 9-continued

Depth and Permeability of Twin Core Samples

| | Amott & USBM Samples | | RIC Samples | |
|---|---|---|---|---|
| Formation | Depth, ft | Perm, md | Depth, ft | Perm, md |
| YZ3A | XX28.00 | 9 | XX28.50 | 21 |
| YZ3A | XX61.00 | 3 | XX60.82 | 19 |
| YZ3C | XX26.00 | 10 | XX26.61 | 25 |
| YZ3C | XX41.00 | 21 | XX40.80 | 34 |
| YZ3C | XX53.00 | 64 | XX52.65 | 46 |
| YZ3C | XX61.00 | 38 | XX61.35 | 37 |

Table 10 presents the properties of the fluids of the four formations.

TABLE 10

Physical Properties of Crude Oil and Formation Water

| Sample | Density g/cm$^3$ | Viscosity, cp | Surface Tension, dyne/cm | IFT(Crude/Brine), Dyne/cm |
|---|---|---|---|---|
| YZ1A_crude | 0.8675 | 2.3744 | 30.94 | 33.76 |
| YZ1A_Fm Water | 1.1393 | 1.3951 | 71.95 | |
| YZ2_Crude | 0.8598 | 2.3539 | 31.03 | 33.24 |
| YZ2Fm Water | 1.1213 | 1.2256 | 72.11 | |
| YZ3A_Crude | 0.8421 | 1.2132 | 31.42 | 34.21 |
| YZ3A_Fm Water | 1.1409 | 1.4291 | 72.19 | |
| YZ3C_Crude | 0.8692 | 2.3905 | 30.85 | 34.03 |
| YZ3C_Fm Water | 1.1399 | 1.2096 | 72.20 | |

The modified USBM test at ambient conditions was followed to determine the Amott-Harvey and USBM wettability indices. The API published procedure stipulates centrifuge capillary pressures up to 10 psi, however, this may be insufficient to de-saturate low permeability samples. Therefore, pressures up to 15 psi were utilized in these experiments.

Figure 20:
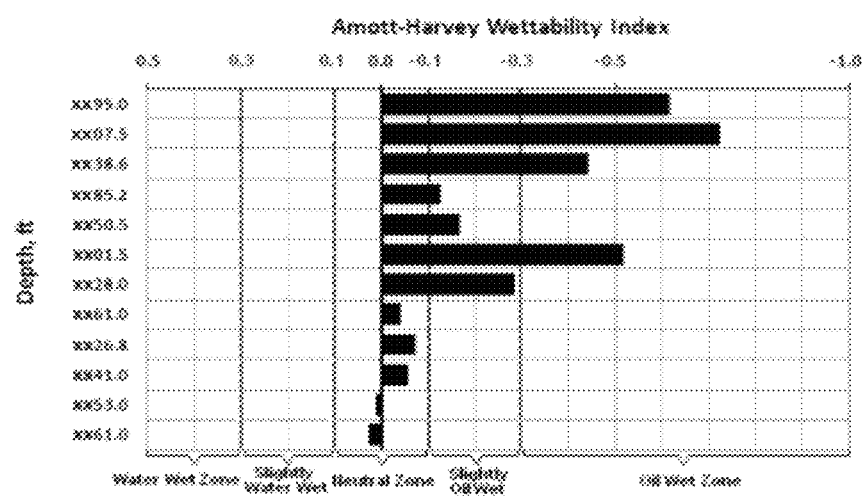
FIG. 20 shows the Amott Harvey Indices for the tested 12 plugs, according to an embodiment herein.
Figure 21:
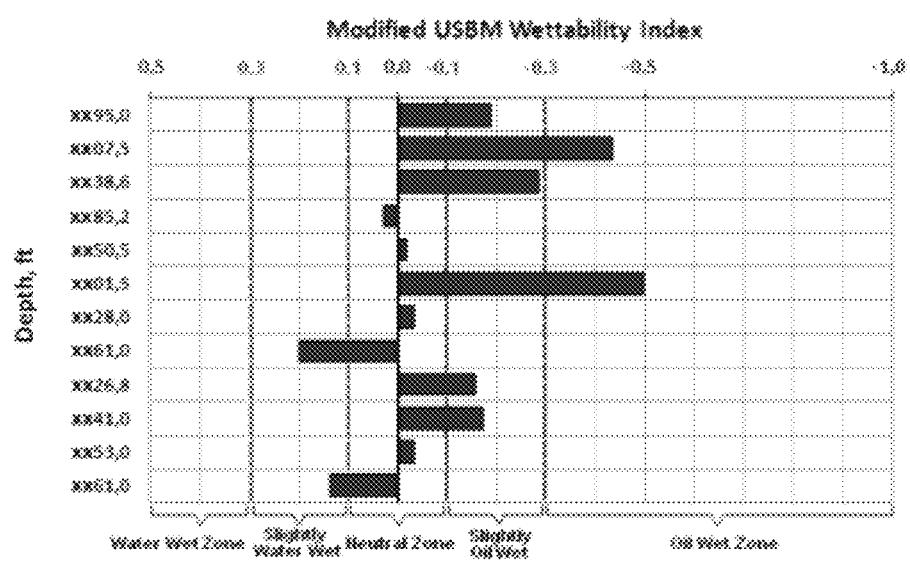
FIG. 21 shows the USBM Indices for the same plugs, according to an embodiment herein.

FIG. 20 shows the Amott Harvey Indices for the tested 12 plugs, according to an embodiment herein. FIG. 21 shows the USBM Indices for the same plugs, according to an embodiment herein. The wettability cut off criterion adopted from Okasha was used to classify the USBM indices for both Amott-Harvey index as well as USBM index. With respect to FIG. 20 and FIG. 21, the index range −0.1 to +0.1 indicates neutral or mixed-wet, the range +0.1 to +0.3 indicate slight water-wetness, while the range +0.3 to +1.0 indicate water-wetness. The range −0.1 to −0.3 indicates slight oil-wetness, and the range −0.3 to −1.0 indicates oil-wetness. According to FIG. 20, the Amott-Harvey indices indicated either neutral, slight to oil-wetness and according to FIG. 21, the USBM indices indicated neutral-wetness, slight water or oil-wetness, and oil-wetness.

Example 7

Results of the Rise in Core Wettability Method on a Carbonate Core

After measuring the physical properties, each core plug was divided into three or more core samples of 3.8 cm average diameter and 1.5 cm length each. The following measurements were done: The mid core sample of the core plug was utilized to determine the constant C.

Figure 22:
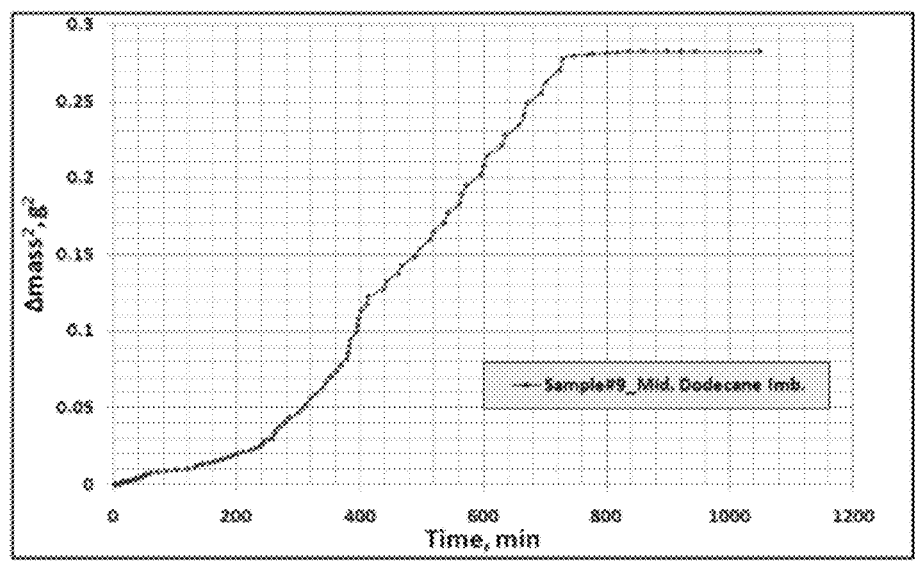
FIG. 22 shows the RIC Dodecane imbibition curve for one of the Carbonate Core Samples, according to an embodiment herein.

FIG. 22 shows the RIC Dodecane imbibition curve for one of the Carbonate Core Samples, according to an embodiment herein. Using the curve obtained in FIG. 22, the slope was determined. After determining the slope of the dodecane RIC curve, the average constant, C, was determined to be 8.634× $10^{11}$ μm. This average was calculated after considering the uncertainty in the value of the constant C as a function of the uncertainty of the slope of the dodecane imbibition curve. The top and bottom core plugs were utilized to measure the wettability of the subject carbonate core sample. One core sample was flushed with formation water removing any gas and movable oil. The core sample was then subjected to the RIC oil imbibition. The second core sample was flushed by crude oil to flush out gas and movable water, and then subjected to RIC water imbibition. The imbibition curves were obtained for the carbonate core samples.

Figure 23:
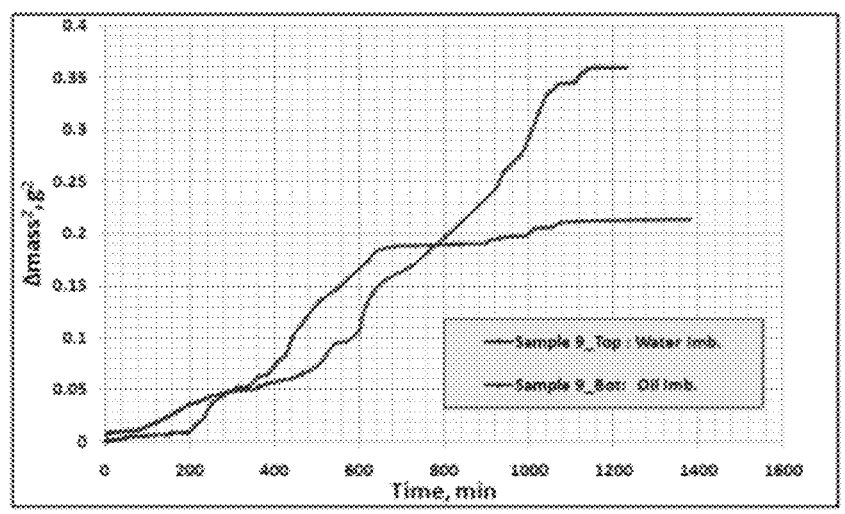
FIG. 23 shows the RIC Imbibition Curves for carbonate core samples imbibed with water (top) and carbonate core sample imbibed with oil (bottom) to determine the Contact Angle for one of the Carbonate Core Samples, according to an embodiment herein.

FIG. 23 shows the RIC Imbibition Curves for carbonate core samples imbibed with water (top) and carbonate core sample imbibed with oil (bottom) to determine the Contact Angle for one of the Carbonate Core Samples, according to an embodiment herein. Contact angle calculation was made with both RIC imbibition curves considering uncertainty in the slope of the imbibition curves as well as uncertainty in the constant C value. Table 11 presents the range of the contact angle values considering minimum, average and maximum possible values for C and the RIC imbibition slope. The range of the contact angles varied between 114° and 124°.

bination of Chilingar et al. and Morrow wettability cutoff criteria was adopted. With respect to FIG. 24, the contact angle range 80° to 100° indicates neutral-wetness, the range 100-133° indicates slight oil-wetness, and the range 133° to 160° indicates oil-wetness while the range 160° to 180° indicates strongly oil-wetness. The range 62°-80° indicates slight water-wetness, the range 200-62 indicates water-wetness, and while the range 0° to 20° indicates strong water-wetness. The results showed that most of the core samples were either slightly oil-wet or oil-wet. Some of the slightly oil wet samples could cross to neutral wetness if uncertainty is considered. Since the method entails two RIC imbibition experiments, one with oil and the other one with water, it provides an indication of mixed wettability if any. Oil-wet samples showed very little water imbibition indicating mostly oil-wetness with some mixed-wetness. Slightly oil-wet samples, experienced more water imbibition indicating more of mixed to slight oil wet cores.

The results obtained by the USBM wettability tests, Amott-Harvey tests and RIC tests were compared. Table 12 summarizes the results of both modified USBM wettability tests as well as that of the RIC tests.

TABLE 12

Wettability Determined by Modified USBM Testing Method versus the RIC Wettability Testing Method

| Reservoir Formation | Reservoir, Depth, ft | Amott-Harvey | Wettability classification | USBM Index | Wettability Classification | Reservoir Depth, ft | RIC contact Angle | Wettability Classification |
|---|---|---|---|---|---|---|---|---|
| YZ1A0 | XX95.00 | −0.614 | Oil Wet | −0.188 | Slight Oil Wet | XX94.80 | 125 | Slight Oil Wet |
| YZ1A0 | XX07.50 | −0.722 | Oil Wet | −0.434 | Oil Wet | XX07.30 | 140 | Oil Wet |
| YZ1A0 | XX38.60 | −0.442 | Mod Oil wet | −0.285 | Slight Oil Wet | XX38.40 | 114 | Slight Oil Wet |
| YZZ | XX85.20 | −0.124 | Slight Oil Wet | 0.03 | Neutral Wet | XX85.75 | 110 | Slight Oil Wet |
| YZZ | XX50.50 | −0.168 | Slight Oil Wet | −0.017 | Neutral wet | XX50.30 | 114 | Slight Oil Wet |
| YZZ | XX01.50 | −0.516 | Oil Wet | −0.499 | Oil Wet | XX02.00 | 141 | Oil Wet |
| YZ3A | XX28.00 | −0.282 | Slight Oil wet | −0.035 | Neutral Wet | XX28.50 | 117 | Slight Oil wet |
| YZ3A | XX61.00 | −0.041 | Neutral Wet | 0.2 | Slight Water wet | XX60.82 | 111 | Slight Oil wet |
| YZ3C | XX26.80 | −0.071 | Neutral Wet | −0.157 | Slight Oil wet | XX26.61 | 117 | Slight Oil wet |
| YZ3C | XX41.00 | −0.055 | Neutral Wet | −0.173 | Slight Oil wet | XX40.80 | 118 | Slight Oil wet |
| YZ3C | XX53.00 | −0.010 | Neutral Wet | −0.033 | Neutral Wet | XX52.65 | 113 | Slight Oil wet |
| YZ3C | XX61.00 | −0.026 | Neutral Wet | 0.138 | Slight Water wet | XX61.35 | 112 | Slight Oil wet |

TABLE 11

Uncertainty Analysis of RIC Contact Angle

| Top (Water Imbibition) | | | | Bottom (Oil Imbibition) | | | |
|---|---|---|---|---|---|---|---|
| | C | | | | C | | |
| Slope | Min | Max | Avg | Slope | Min | Max | Avg |
| Min | 119.10 | 115.91 | 117.27 | Min | 117.30 | 114.33 | 115.61 |
| Max | 120.91 | 117.41 | 118.94 | Max | 124.29 | 120.40 | 122.06 |
| Avg | 119.73 | 116.45 | 117.85 | Avg | 118.92 | 115.75 | 117.11 |

Figure 24:
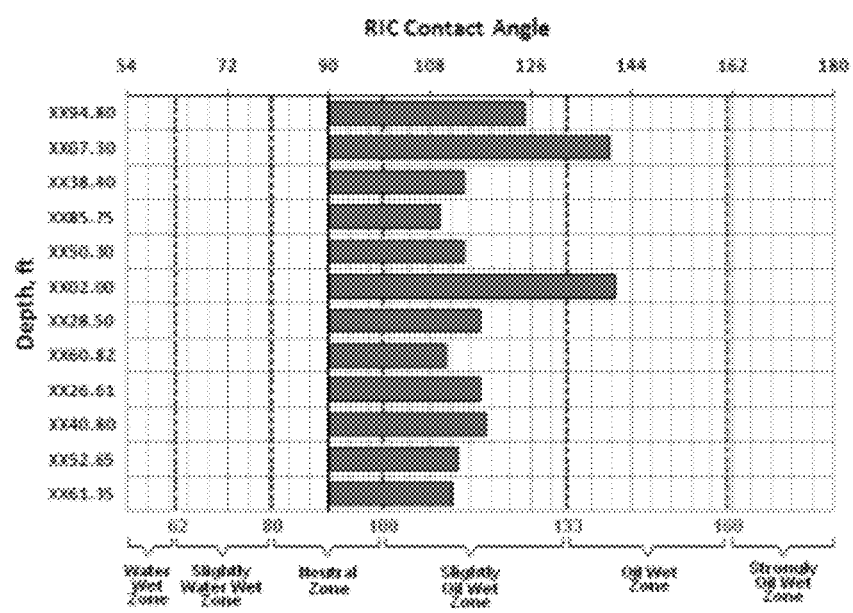
FIG. 24 shows the average contact angle of the tested 12 twin core plugs, according to an embodiment herein.

FIG. 24 shows the average contact angle of the tested 12 twin core plugs, according to an embodiment herein. A com- With respect to table 12, RIC labeled all samples as oil wet to slightly oil wet. Amott-Harvey and USBM results were more varied with four or more samples occupying the neutral wettability zone. Two of the USBM samples are classified as slightly water wet. Both AMOTT and USBM show a decrease in oil wetness with increasing depth, while RIC showed a weaker trend. The correlation between the RIC wettability classifications with Amott-Harvey is better than with USBM. The differences between AMOTT and RIC are for samples AMOTT labeled as neutral wet. One of the limitations of the Amott-Harvey is near neutral wetness. Further the studies need to be conducted of the RIC method particularly in water zones and close to the oil water contact to judge the reliability of the measurement.

The new Reservoir Rock wettability measurement technique is invented based on modified version of the Washburn equation, which is normally used to determine wettability of liquid/air/powder system. The Experimental Setup was designed and assembled to perform the required measurements. RIC concept was proved. The results of the RIC technique are found to be repeatable for the same conditions. This is found true for three tested wettability bands of neutrally wet, slightly water wet, and oil wet rocks. The variation in the calculated contact angles by RIC technique due to the uncertainties is found to be limited and does not change the results drastically. The performance of the RIC technique was tested against the mostly used oil industry wettability measurement techniques of Amott-Harvey and USBM techniques. The experiments were performed on twin core samples and comparable results were found. Although performed on the same core samples, a weak correlation is found between the two mostly used industry techniques of Amott-Harvey and the USBM indices. The USBM indices are not consistently lower or higher than the Amott-Harvey, but it could be random at times. This is reflected on the wettability classification. Some oil samples by Amott-Harvey would classify as slight oil-wet for USBM and vice versa. The correlation between the RIC wettability classification matches better with Amott-Harvey Indices and better than USBM indices. The difference between RIC and the other two methods is consistently found at AMOTT/USBM labeled neutral-wetness.

Although the embodiments have been described in some detail by way of illustration and example for the purposes of clarity of understanding, it is clearly not limited thereby and the embodiments encompass any changes and modifications that may be practiced within the scope of the appended claims by ones skilled in the art.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the embodiments with modifications. However, all such modifications are deemed to be within the scope of the claims. It is also to be understood that the following claims are intended to cover all of the generic and specific features of the embodiments described herein and all the statements of the scope of the embodiments, which as a matter of language might be said to fall there between.

What is claimed is:

1. A method for determining Reservoir Rock wettability comprising steps of:
    generating and utilizing core samples, wherein a core sample is generated by dividing a core plug into a plurality of core samples of a preset size and wherein the preset size of each core sample in the plurality of core samples is an average diameter of 3.8 cm and a length of 1.5 cm;
    sealing a side of the core sample with an epoxy resin, wherein the side of the core sample is sealed to ensure a one-dimensional liquid penetration into the core sample;
    mounting a hook on a top side of the core sample;
    saturating the core sample with a first reservoir fluid;
    connecting the saturated core sample to a high precision balance, wherein the saturated core sample is connected using a thin rope;
    taking a second reservoir fluid in an imbibition beaker;
    hanging the saturated core sample over the second reservoir fluid contained in the imbibition beaker, wherein the saturated core sample is hanged using a thread and wherein the saturated core sample is hanged in a way such that a bottom part of the saturated core sample barely touches the second reservoir fluid;
    commencing an imbibition process for the hanged and saturated core sample;
    monitoring a change in a mass of the hanged and saturated core sample over a period of time as imbibitions taking place to obtain a data and wherein the data is a square of the change in the mass of the hanged and saturated core sample over a period of time;
    generating a curve using the obtained data by plotting a square of the change in the mass of the hanged and saturated core sample with respect to time;
    calculating a slope of the generated curve;
    computing a value of a rock constant for the core sample; and
    applying the calculated slope of the generated curve and the computed value of a rock constant for the core sample in a modified form of Washburn equation to compute a value of a contact angle;
    wherein the computed value of contact angle represents a wettability of the core sample and in turn represents the wettability of a reservoir rock from which the core plug is generated.

2. The method according to claim 1, wherein the constant is a characteristic of a core sample.

3. The method according to claim 2, wherein the step of determining the constant C comprises:
    generating twin core samples;
    saturating one of the generated twin core samples with air;
    imbibing the saturated twin core sample with a reference fluid and wherein the reference fluid has low surface energy and wherein the reference fluid is Dodecane;
    monitoring a change of a mass of the twin core sample with respect to time using a high precision balance;
    plotting a curve using a square of the change of the mass of the twin core sample with respect to time;
    determining a slope of a straight line part of the plotted curve;
    determining a value of the constant C for the core sample by applying the determined value of the slope of the straight line part of the plotted curve and by applying a value of the contact angle in a modified Washburn equation, wherein the value of contact angle is assumed to be zero since the reference fluid completely wets the core sample in presence of air.

4. The method according to claim 1, wherein the first reservoir fluid is water.

5. The method according to claim 1, wherein the second reservoir fluid is oil.

6. The method according to claim 1, wherein the reservoir rock sample is completely water wet at a contact angle of 0°, weakly water wet to weakly oil wet between the contact angles of 62° to 133°, completely oil wet at a contact angle of 180° and neutral at a contact angle of 90°.

7. The method according to claim 1, wherein the method is used for Rock/liquid/liquid System.

8. A method for determining wettability characteristics of reservoir core samples comprising steps of:
- starting with a preserved core plug;
- generating a first twin core sample and a second twin core sample, and wherein the generated first twin core sample is used to determine a constant of a modified Washburn equation, and wherein the generated second twin core sample is used to determine wettability of a rock;
- cleaning the generated first twin core sample;
- drying the cleaned first twin core sample;
- saturating the dried first twin core sample with air;
- imbibing the air saturated first twin core sample with a low energy fluid, wherein the low energy fluid is Dodecane;
- monitoring a change in a mass of the first twin core sample with respect to time as dodecane imbibes into the first twin core sample;
- generating a curve by plotting a square of the change in the mass of the first twin core sample with respect to time;
- determining a slope value of the generated curve;
- calculating a value of a rock constant by applying the determined slope value of the generated curve and a contact angle of the first twin core sample for the reference fluid in a modified Washburn Equation, wherein the applied contact value of the first twin core sample for the reference fluid is equal to zero as the reference fluid is a dodecane and the dodecane wets the first twin core sample completely;
- saturating the second twin core sample with a first reservoir fluid, wherein the second twin core sample is saturated in the first reservoir fluid completely;
- imbibing the saturated second twin core sample with a second reservoir fluid;
- monitoring a change in a core mass of the second twin core sample with respect to time as the second reservoir fluid is imbibed into the second twin core sample;
- calculating a square of the change in the mass of the second twin core sample with respect to time;
- generating a curve for the second twin core sample by plotting the calculated square of the change in the mass of the second twin core sample with respect to time;
- calculating a slope of the generated curve for the second twin core sample;
- calculating a value of contact angle by applying the calculated slope of the generated curve for the second twin core sample and the computed value of a rock constant for the first twin core sample in a modified form of Washburn equation; and
- wherein the calculated value of contact angle represents a wettability of the second twin core sample and in turn corresponds to a wettability of a reservoir rock from which the core plug is extracted.

9. The method according to claim 8, wherein the change in square of the mass of the core sample with respect to time is monitored using a high precision balance and a computer.

10. The method according to claim 8, wherein the wettability characteristics is determined on the basis of the contact angle.

11. The method according to claim 8, wherein the contact angle is determined using the modified Washburn equation.

12. The method according to claim 8, wherein the reservoir rock sample is completely water wet at a contact angle of 0°, weakly water wet to weakly oil wet between contact angles of 62° to 133°, completely oil wet at a contact angle of 180° and neutral at a contact angle of 90°.

13. The method according to claim 8, wherein the method is used for Rock/liquid/liquid System.

14. The method according to claim 11, wherein the modified form a Washburn equation for a Rock/liquid/liquid System is derived from a Washburn equation provided for calculating a penetration rate for a liquid/air/rock system.

15. The method according to claim 14, wherein the step of deriving the modified form of the Washburn equation for a Rock/liquid/liquid System comprises:
- acquiring a Washburn equation for a rock/liquid/liquid system, and wherein Washburn equation for a rock/liquid/liquid system is represented by $$t = \frac{\mu}{C \cdot \rho^2 \gamma \cos\theta} \cdot m^2, \tag{1}$$

wherein equation (1) is a Washburn equation for liquid/air/rock system, and wherein t is a penetration rate of a liquid into a porous sample, and wherein is a viscosity of the liquid, and wherein $\rho$ is a density of the liquid, and wherein $\gamma$ is a surface tension of the liquid, and wherein $\theta$ is a contact angle made by the liquid, and wherein m is a mass of the liquid penetrated into the porous sample and wherein C is a Constant of Characterization of the porous sample;

evaluating a value of $\gamma_{os}$ using a young's equation for a rock surface/oil/air system and a value of $\gamma_{ws}$ using a young's equation for a rock surface/water/air system and wherein the young's equation for a liquid/liquid/rock system is represented by equation (2)

$$\gamma_{ow} \cos\theta = \gamma_{os} - \gamma_{ws} \tag{2},$$

wherein $\gamma_{ow}$ is a surface tension between oil and water system, and wherein $\gamma_{os}$ is a surface tension between oil and solid system, and wherein $\gamma_{ws}$ is a surface tension between water and solid system;

substituting the evaluated value of $\gamma_{os}$ using a young's equation for a rock surface/oil/air system and value of $\gamma_{ws}$ using a young's equation for a rock surface/water/air system and substituting in equation (2) to obtain an equation (3), and wherein the equation (3) is $$\cos\theta_{wo} = \frac{(\gamma_o \cos\theta_o) - (\gamma_w \cos\theta_w)}{\gamma_{wo}}; \tag{3}$$

rearranging equation (1) to factor out $\gamma_{LV}$ to obtain an equation (4), and wherein $\gamma_{LV}$ is a liquid-vapor surface tension, and $$\gamma_{LV} = \frac{\mu}{C \cdot \rho^2 \cdot \cos\theta} \cdot \frac{m^2}{t}; \tag{4}$$

realizing that $\gamma_{LV}$ (liquid-vapor surface tension) is equivalent to $\gamma_o$ (oil-air surface tension), or $\gamma_w$ (water-air surface tension), substitute equation 4 in equation 3 and cancelling out similar terms to obtain equation (5), and wherein equation (5) is $$\cos\theta_{wo} = \frac{\left(\frac{m^2 \cdot \mu_o}{C\rho_o^2 t}\right) - \left(\frac{m^2 \cdot \mu_w}{C\rho_w^2 t}\right)}{\gamma_{wo}}; \quad (5)$$

wherein $\gamma_{LV}$ is liquid-vapor surface tension, and wherein $\gamma_o$ is oil-air surface tension and wherein $\gamma_w$ is water-air surface tension, and wherein $\mu_o$ is viscosity of oil, and wherein $\mu_w$ is viscosity of water, and wherein $\cos\theta$ is contact angle between water and oil;

representing a relation ship between a mass of water imbibed into the core sample and a mass of oil imbibed in the core sample with a equation (6), wherein the equation (6) is $\rho_w g V_w = \rho_o g V_o$;

wherein $\rho_w$ is density of water and $V_w$ is volume of water imbibed, wherein $\rho_o$ is density of oil and $V_o$ is volume of oil imbibed, wherein the amount of water imbibed and amount of oil imbibed under gravity are same; and wherein air behaves as a strong non-wetting phase in both of a oil/air/solid and a water/air/solid systems, thereby indicating that both oil and water behaves as a strong wetting phases, resulting in an equal air/oil and air/water capillary forces for a same porous media and for a given pore size distribution, and wherein a mass change of a core sample due to a water imbibition is equal to a mass change of a core sample as a due to an oil imbibition because water or oil penetration of the porous media at any time is a function of a balance between a gravity and a capillary forces, and wherein a mass of water imbibed into a core sample is approximately equal to a mass of oil imbibed in the core sample core samples of a same rock type and dimensions, and for equal capillary forces;

cancelling out g in equation (6) represented $\rho_w g V_w = \rho_o g V_o$ to obtain an equation (7), wherein equation (7) is $\rho_w V_w = \rho_o V_o$ to acquire an equation (8), and wherein equation (8) is $$m_w = m_o \quad (8),$$

wherein $m_w$ is mass of water and wherein $m_o$ is mass of oil;

factoring out $C \cdot m^2/t$ from equation (5) to obtain equation (9), wherein equation (9) is a modified Washburn equation, and wherein the modified Washburn equation is $$\cos\theta_{12} = \frac{(\mu_1 \cdot \rho_2^2) - (\mu_2 \cdot \rho_1^2)}{\rho_1^2 \rho_2^2 \cdot C \cdot \gamma_{L2L1}} \cdot \frac{m^2}{t}$$

wherein $\theta_{12}$ is the contact angle of liquid/liquid/rock system, and wherein $\mu_1$ is a Viscosity of oil phase, and wherein $\rho_2$ is a Viscosity of water phase, and wherein $\rho_1$ is a density of oil phase in g/cm$^3$, and wherein $\rho_2$ is a density of water phase in g/cm$^3$, and wherein m is a mass of fluid penetrated into a porous rock in g, and wherein t is a time in min, and wherein $\gamma_{L2L1}$ is a surface tension between a oil and a water in dyne/cm, and C is a Characteristic Constant, of the porous rock.

* * * * *